United States Patent
Son et al.

(10) Patent No.: US 12,421,250 B2
(45) Date of Patent: Sep. 23, 2025

(54) TERNARY PHOTOACTIVE LAYER COMPOSITION AND ORGANIC SOLAR CELL COMPRISING SAME

(71) Applicant: KOREA INSTITUTE OF SCIENCE AND TECHNOLOGY, Seoul (KR)

(72) Inventors: Hae Jung Son, Seoul (KR); Sungmin Park, Seoul (KR); So Hyun Park, Seoul (KR); Hyunjung Jin, Seoul (KR); Hyeonggeun Yu, Seoul (KR); Jai Kyeong Kim, Seoul (KR); Seongwon Yoon, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 608 days.

(21) Appl. No.: 17/884,154

(22) Filed: Aug. 9, 2022

(65) Prior Publication Data
US 2023/0227473 A1   Jul. 20, 2023

(30) Foreign Application Priority Data
Jan. 20, 2022 (KR) .......... 10-2022-0008493

(51) Int. Cl.
*C07D 513/22* (2006.01)
*H10K 30/30* (2023.01)

(52) U.S. Cl.
CPC .......... *C07D 513/22* (2013.01); *H10K 30/30* (2023.02)

(58) Field of Classification Search
CPC .................................................. C07D 513/22
See application file for complete search history.

(56) References Cited

FOREIGN PATENT DOCUMENTS

KR    10-2021-0015883 A    2/2021

OTHER PUBLICATIONS

Yu, Han, et al. "Fluorinated end group enables high-performance all-polymer solar cells with near-infrared absorption and enhanced device efficiency over 14%." *Advanced Energy Materials* 11.4 (2021). 2003171. pp 1-9.
Wang, Wei, et al. "Controlling molecular mass of low-band-gap polymer acceptors for high-performance all-polymer solar cells." *Joule* vol. 4. Issue 5 (2020). pp. 1069-1086.
Sun, Rui, et al. "Achieving over 17% efficiency of ternary all-polymer solar cells with two well-compatible polymer acceptors." Joule 5.6., 2021, (73 pages).

*Primary Examiner* — John S Kenyon
(74) *Attorney, Agent, or Firm* — NSIP Law

(57) ABSTRACT

The present disclosure relates to a ternary photoactive layer composition and an organic solar cell including the same. According to the present disclosure, excessive crystal growth and aggregation can be prevented during large-area coating of a photoactive layer, uniform morphology can be achieved without significant phase separation, an organic solar cell with superior photovoltaic cell characteristics can be realized, and superior performance may be maintained even after long-term exposure to heat by preventing the morphological change of the photoactive layer.

16 Claims, 6 Drawing Sheets

PY-T1

PY-T2

PY-P2

TERNARY PHOTOACTIVE LAYER COMPOSITION AND ORGANIC SOLAR CELL COMPRISING SAME

CROSS-REFERENCE TO RELATED APPLICATION

This application claims priority to Korean Patent Application No. 10-2022-0008493 filed on Jan. 20, 2022, in the Korean Intellectual Property Office, and all the benefits accruing therefrom under 35 U.S.C. § 119, the contents of which in its entirety are herein incorporated by reference.

BACKGROUND

1. Field

The present disclosure relates to a ternary photoactive layer composition and an organic solar cell including the same. More particularly, it relates to an electron acceptor compound which is added to a photoactive layer of an organic solar cell including an electron donor and an electron acceptor so as to improve morphology by preventing excessive crystal growth and aggregation of the photoactive layer, thereby allowing area enlargement and improving solar cell characteristics, and a ternary photoactive layer composition containing the same.

2. Description of the Related Art

A solar cell is a photovoltaic conversion device that converts solar energy into electrical energy. It is drawing a lot of attentions as a next-generation energy resource. Solar cells can be largely classified into an inorganic solar cell and an organic solar cell. Depending on the structure of a photoactive layer, the organic solar cells are classified into a bilayer p-n junction type consisting of separate layers of a p-type semiconductor and an n-type semiconductor, and a bulk heterojunction type wherein a p-type semiconductor and an n-type semiconductor are mixed to form a single layer.

In general, a unit cell of the organic solar cell exhibits a power conversion efficiency of about 18%, but the active area of the organic solar cell is only about 0.1 $cm^2$. Although some researches have succeeded in achieving large-area organic solar cells with an area of 1 $cm^2$ and a power conversion efficiency of 14-16%, but they were limited in that a spin coating process was used. Although the spin coating process is used widely due to fast coating speed and high reproducibility, it consumes a large amount of a coating solution and area enlargement is difficult.

For commercialization of solar cells, meniscus coating similar to roll-to-roll printing needs to be used. But, when meniscus coating is used, the power conversion efficiency of the organic solar cell is decreased rapidly to about 9-14%.

Accordingly, for preparation of a large-area organic solar cell, development of a new photoactive layer additive which can improve the performance and efficiency of a photoactive layer, regarded as the important cause of low power conversion efficiency, by providing optimized morphology between an electron donor and an electron acceptor for effective charge generation and transport is necessary.

REFERENCES OF THE RELATED ART

Patent Documents

Patent document 1. Korean Patent Publication No. 10-2021-015883.

SUMMARY

The present disclosure is directed to providing an electron acceptor compound which can control the morphology of a photoactive layer by inhibiting aggregation and crystal growth that may occur during meniscus coating of an electron donor material and an electron acceptor material, and a ternary photoactive layer composition for an organic solar cell containing the same.

The present disclosure is also directed to providing an organic solar cell having uniform morphology without excessive crystal growth or aggregation during area enlargement through meniscus coating.

The present disclosure provides a ternary photoactive layer composition for an organic solar cell, which contains: a first electron acceptor material; a second electron acceptor compound represented by Chemical Formula I; and an electron donor material:

[Chemical Formula I]

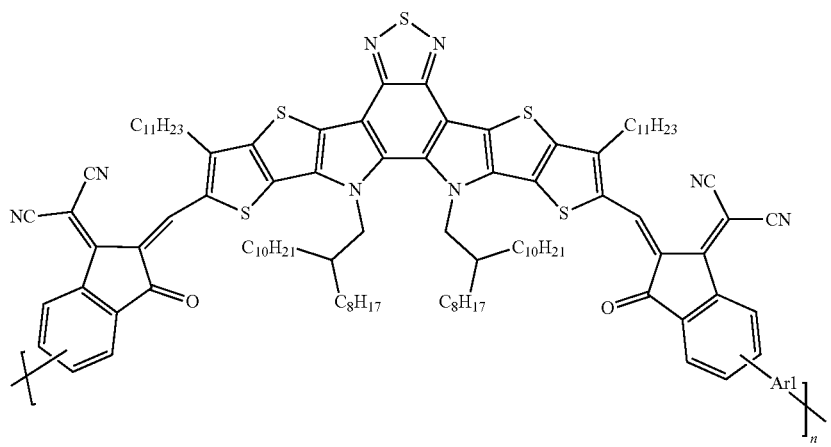

wherein Ar$_1$ is one selected from [Structural Formula 1], and n is an integer in a range from 1 to 1000:

[Structural Formula 1]

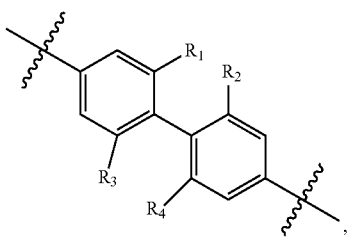

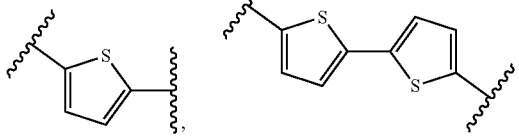

wherein each of R$_1$, R$_2$, R$_3$ and R$_4$, which are identical to or different from each other, is independently one selected from hydrogen, a halogen and a C$_{1-4}$ alkyl group.

The first electron acceptor material and the second electron acceptor compound may be mixed at 50-150 parts by weight and 1-50 parts by weight, respectively, based on 100 parts by weight of the electron donor material.

Chemical Formula I may be one selected from Chemical Formulas Ia to Ic:

[Chemical Formula Ia]

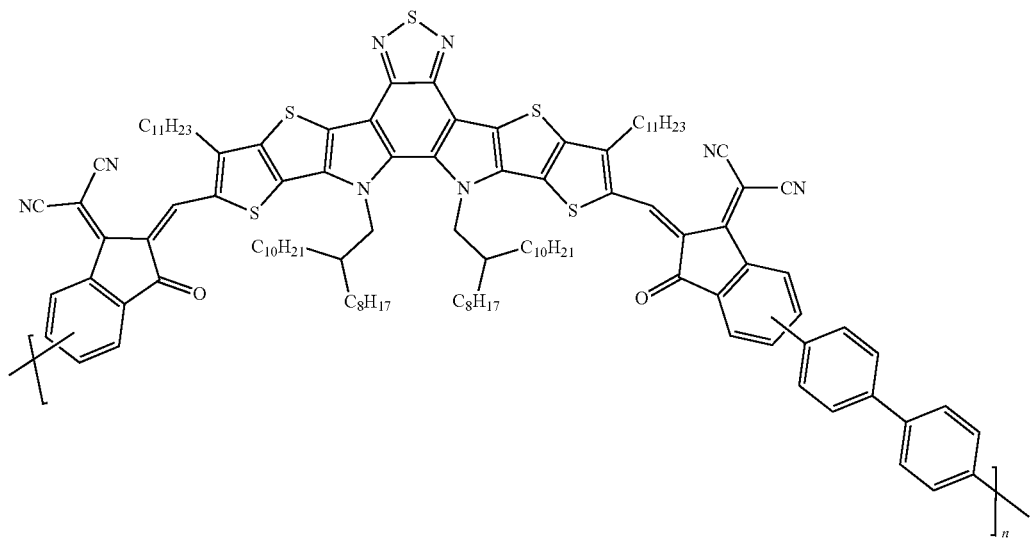

[Chemical Formula Ib]

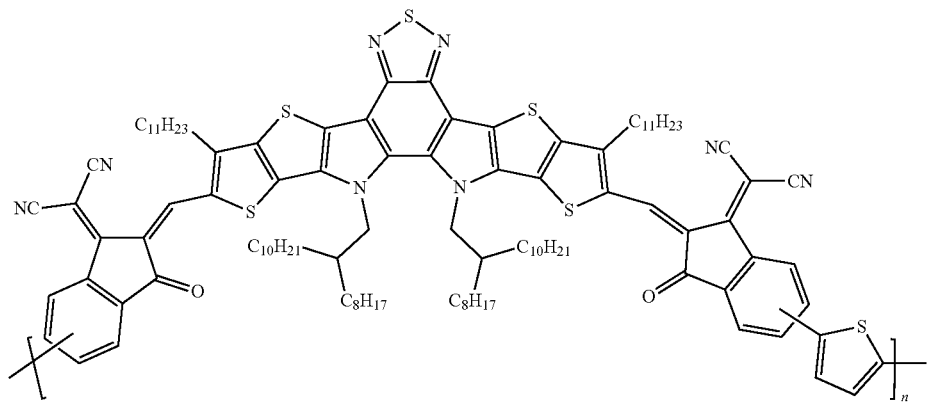

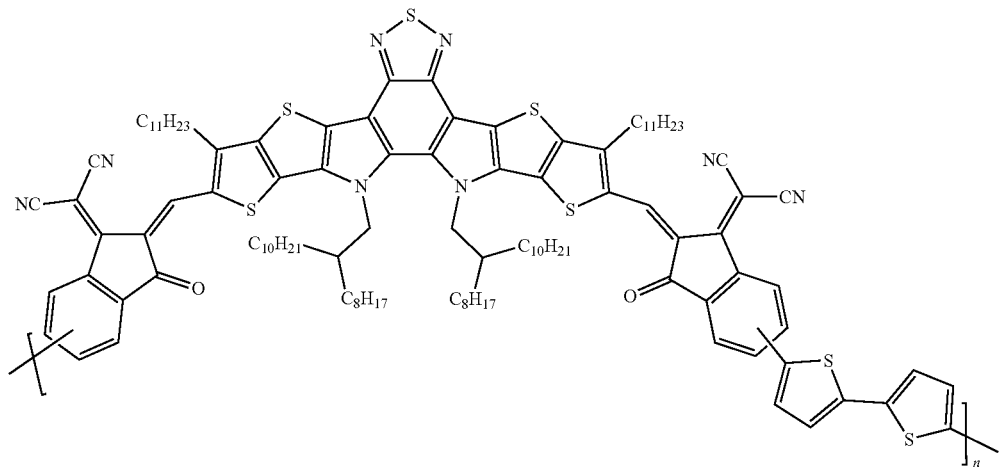

wherein n is an integer in a range from 1 to 1000.
Chemical Formula I may be Chemical Formula Ia:

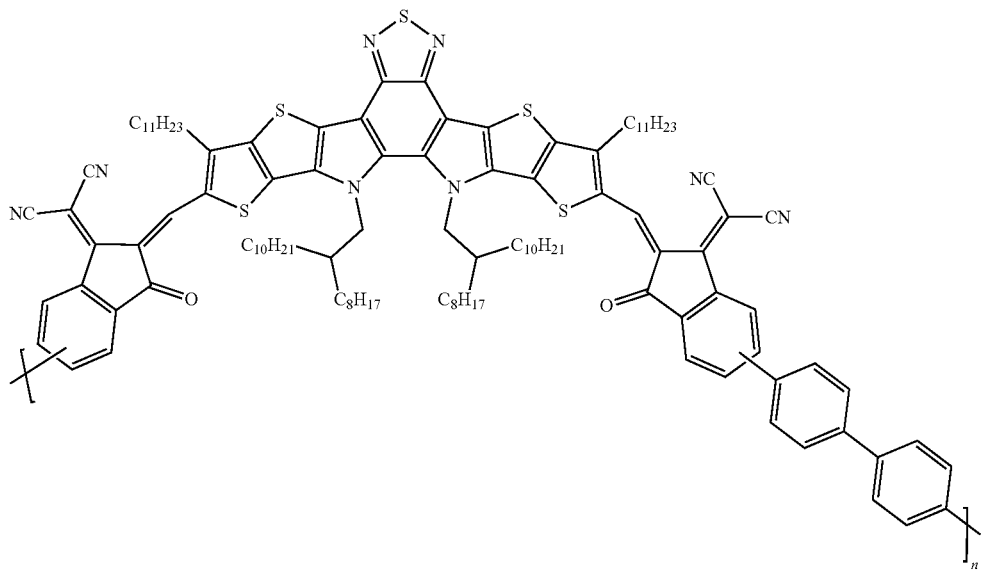

wherein n is an integer in a range from 1 to 1000.

The first electron acceptor material may be one or more selected from a group consisting of fullerene, 6,6-phenyl-$C_{61}$-butyric acid methyl ester (PCBM(C61)), PCBM(C60), PCBM(C70), PCBM(C71), PCBM(C76), PCBM(C80), PCBM(C82), indene-$C_{60}$ bisadduct (ICBA), 6,6-phenyl-C61-butyric acid cholesteryl ester (PCBCR), polybenzimidazole, perylene, poly[[N,N'-bis(2-octyldodecyl)-napthalene-1,4,5,8-bis(dicarboximide)-2,6-diyl]-alt-5,5'-(2,2'-bithiophene)] (NDI2OD-T2), naphthalene diimide (NDI)-selenophene copolymer (PNDIS-HD), poly[(E)-2,7-bis(2-decyltetradecyl)-4-methyl-9-(5-(2-(5-methylthiophen-2-yl)vinyl)thiophen-2-yl)benzo[lmn][3,8]phenanthroline-1,3,6,8(2H,7H)-tetraone] (PNDI-TVT), poly[[N,N'-bis(2-hexyldecyl)naphthalene1,4,5,8-bis(dicarboximide)-2,6-diyl]-alt-5,5'-thiophene] (PNDI2HD-T), 3,9-bis(2-methylene-(3-(1,1-dicyanomethylene)-indanone))-5,5,11,11-tetrakis(4-hexylphenyl)-dithieno[2,3-d:2',3'-d']-s-indaceno[1,2-b:5,6-b']dithiophene (ITIC), 3,9-bis(2-methylene-(3-(1,1-dicyanomethylene)-indanone))-5,5,11,11-tetrakis(5-hexylthienyl)-dithieno[2,3-d:2',3'-d']-s-indaceno[1,2-b:5,6-b']dithiophene (ITIC-Th), 2,7-bis(3-dicyanomethylene-2Z-methylene-indan-1-one)-4,4,9,9-tetrahexyl-4,9-dihydro-s-indaceno[1,2-b:5,6-b']dithiophene (IDIC), 3,9-bis(2-methylene-((3-(1,1-dicyanomethylene)-6,7-difluoro)-indanone))-5,5,11,11-tetrakis(4-hexylphenyl)-dithieno[2,3-d:2',3'-d']-s-indaceno[1,2-b:5,6-b']dithiophene (ITIC-4F), 2,2'-((2Z,2'Z)-(((4,4,9-tris(4-hexylphenyl)-9-(4-pentylphenyl)-4,9-dihydro-s-indaceno[1,2-b:5,6-b-dithiophene-2,7-diyl)bis(4-((2-ethylhexyl)oxy)thiophene-5,2-diyl))bis(methanylidene))bis(5,6-difluoro-3-oxo-2,3-dihydro-1H-indene-2,1-diylidene))dimalononitrile (IEICO-4F), 2,2'-((2Z,2'Z)-(((4,4,9-tris(4-hexylphenyl)-9-(4-pentylphenyl)-4,9-dihydro-s-indaceno[1,2-b:5,6-b-dithiophene-2,7-diyl)bis(4-((2-ethylhexyl)oxy)thiophene-5,2-diyl))bis(methanylidene))bis(5,6-dichloro-3-oxo-2,3- dihydro-1H-indene-2,1-diylidene))dimalononitrile (IEICO-4C1), 2,2'-((2Z,2'Z)-((12,13-bis(2-ethylhexyl)-3,9-diundecyl-12,13-dihydro-[1,2,5]thiadiazolo[3,4-e]thieno[2",3":4',5']thieno[2',3':4,5]pyrrolo[3,2-g]thieno[2',3':4,5]thieno[3,2-b]indole-2,10-diyl)bis(methanylidene))bis(5,6-difluoro-3-oxo-2,3-dihydro-1H-indene-2,1-diylidene))dimalononitrile (Y6 or BTP-4F), 2,2'-((2Z,2'Z)-((12,13-bis(2-ethylhexyl)-3,9-diundecyl-12,13-dihydro-[1,2,5]thiadiazolo[3,4-e]thieno[2",3":4',5']thieno[2',3':4,5]pyrrole[3,2-g]thieno[2',3':4,5]thieno[3,2-b]indole-2,10-diyl)bis(methanylidene))bis(5,6-dichloro-3-oxo-2,3-dihydro-1H-indene-2,1-diylidene))dimalononitrile malononitrile (Y7 or BTP-4C1) and Y6-N3.

The electron donor material may be one or more selected from a group consisting of poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]] (PTB7), poly[3,6-bis(5-thiophen-2-yl)-2,5-bis(2-octyldodecyl)pyrrolo[3,4-c]pyrrole-1,4(2H,5H)-dione-2,2'-diyl-alt-thieno[3,2-b]thiophen2,5-diyl] (PDPP2T-TT), poly(3-octylthiophene-2,5-diyl)(P3OT), poly(p-phenylene vinylene) (PPV), poly(dioctyl fluorene), poly[2-methoxy-5-(2-ethylhexyloxy)-1,4-phenylenevinylene] (MEHPPV), poly[2-methoxy-5-(3',7"-dimethyloctyloxy)-1,4-phenylenevinylene] (MDMO-PPV), poly[2,6-(4,4-bis-(2-ethylhexyl)-4H-cyclopenta [2,1-b;3,4-b']dithiophene)-alt-4,7(2,1,3-benzothiadiazole)] (PCPDTBT), poly[4,8-bis(5-(2-ethylhexyl)thiophen-2-yl)-benzo[1,2-b:4,5-b']dithiophene-alt-5-octyl-4H-thieno[3,4-6-c]pyrrole-4,6(5H)-dione] (PBDTTTPD), poly[(2,5-bis(2-hexyldecyloxy)phenylene)-alt-(5,6-difluoro-4,7-di(thiophen-2-yl)benzo-[c][1,2,5]thiadiazole)] (PPDT2FBT), poly(3-hexylthiophene)(P3HT), poly{1-(5-(4,8-bis(5-(2-ethylhexyl)thiophen-2-yl)-6-methylbenzo[1,2-b:4,5-b']-dithiophen-2-yl)thiophen-2-yl)-5,7-bis(2-ethylhexyl)-3-(5-methylthiophen-2-yl)benzo-[1,2-c:4,5-c" ]dithiophene-4,8-dione} (PBDTBDDT) and poly[(2,6-(4,8-bis(5-(2-ethylhexyl-3-fluoro)thiophen-2-yl)-benzo[1,2-b:4,5-b']dithiophene))-alt-(5,5-(1',3'-di-2-thienyl-5',7'-bis(2-ethylhexyl)benzo[1',2'-c:4',5'-c']dithiophene-4,8-dione)] (PBDB-TF, PM6).

The ternary photoactive layer composition may further contain one or more selected from a group consisting of chlorobenzene, chloroform, p-xylene, 1,2-dichlorobenzene, trichlorobenzene, toluene, chloronaphthalene and 1,8-diiodooctane as a solvent.

The solvent may be a mixture of chloroform and 1-chloronaphthalene at a volume ratio of 0.995:0.001-0.01.

The present disclosure also provides an organic solar cell including: a first electrode; an electron transport layer formed on the first electrode; a photoactive layer including the ternary photoactive layer composition and formed on the electron transport layer; a hole transport layer formed on the photoactive layer; and a second electrode formed on the hole transport layer.

The electron transport layer may include one or more selected from ZnO, LiF, $TiO_x$, $TiO_2$, $CsCO_3$ and Ca.

The photoactive layer may have a bulk hetero junction structure in which the first electron acceptor material, the second electron acceptor compound and the electron donor material are mixed.

The orientation and crystallinity of molecules included in the photoactive layer may be controlled by the second electron acceptor compound.

The hole transport layer may include one or more selected from a group consisting of molybdenum oxide ($MoO_2$, $MoO_3$), PEDOT:PSS (poly(3,4-ethylenedioxythiophene) polystyrene sulfonate), tungsten oxide ($WO_3$), nickel oxide and cerium-doped tungsten oxide ($CeWO_3$).

The first electrode may include one or more selected from indium tin oxide (ITO), fluorine tin oxide (FTO), silver (Ag) nanowire and silver nanomesh.

The second electrode may include one or more selected from Au, Fe, Ag, Cu, Cr, W, Al, Mo, Zn, Ni, Pt, Pd, Co, In, Mn, Si, Ta, Ti, Sn, Pb, V, Ru, Ir, Zr, Rh and Mg.

The ternary photoactive layer composition of the present disclosure, which is formed of an electron donor material, a first electron acceptor material and a second electron acceptor compound, is advantageous in that their mixing, orientation and crystallinity can be controlled. In addition, an organic solar cell with superior photovoltaic cell characteristics can be realized as the second electron acceptor compound prevents excessive crystal growth and aggregation of the first electron acceptor material during formation of a large-area thin film through meniscus coating via interaction with the first electron acceptor material and the electron donor material allows control of uniform morphology without significant phase separation.

DETAILED DESCRIPTION

Figure 1:
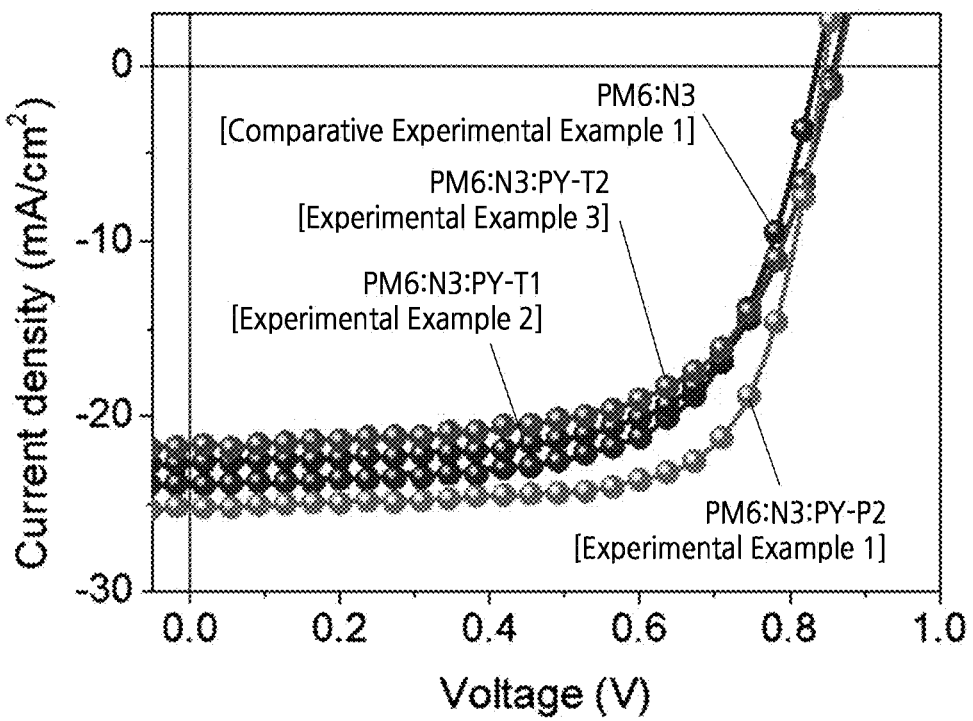
FIG. 1 shows a result of measuring current density depending on voltage for organic solar cells of Experimental Examples 1-3 and Comparative Experimental Example 1.

The present disclosure relates to a ternary photoactive layer composition for an organic solar cell, which contains: a first electron acceptor material; a second electron acceptor compound represented by Chemical Formula I; and an electron donor material.

[Chemical Formula I]

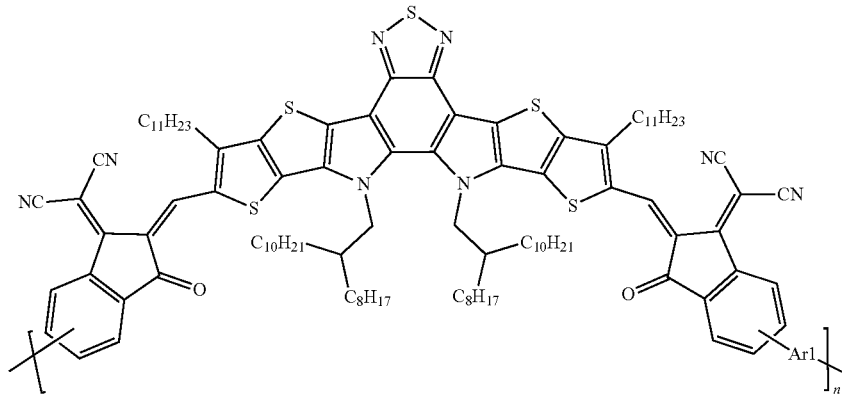

In Chemical Formula I, $Ar_1$ is one selected from [Structural Formula 1] and n is an integer in a range from 1 to 1000.

[Structural Formula 1]

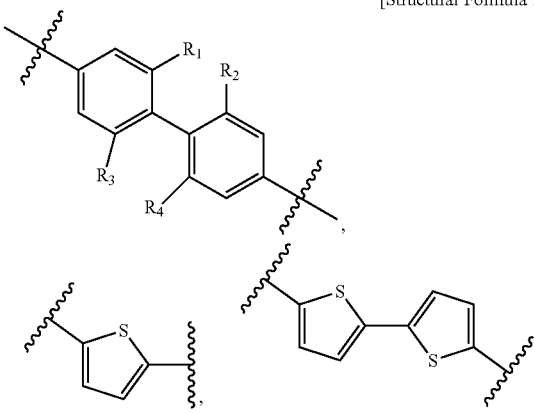

In Structural Formula 1, each of $R_1$, $R_2$, $R_3$ and $R_4$, which are identical to or different from each other, is independently one selected from hydrogen, a halogen and a $C_{1-4}$ alkyl group.

The torsional angle of a functional group positioned at $Ar_1$ in the backbone of Chemical Formula I may be specifically 10-40°, more specifically 15-38°, further more specifically 17-38, even more specifically 30-38° for superior solubility and processability, most specifically 35.8-37.6° for optimized morphology of a ternary photoactive layer and remarkably superior power conversion efficiency.

Specifically, Structural Formula 1 may be Structural Formula 1-1.

[Structural Formula 1-1]

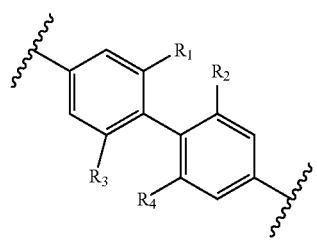

In Structural Formula 1, each of $R_1$, $R_2$, $R_3$ and $R_4$, which are identical to or different from each other, is independently one selected from hydrogen, a halogen and a $C_{1-4}$ alkyl group.

The ternary photoactive layer composition according to the present disclosure, which contains a first electron acceptor material, a second electron acceptor compound represented by Chemical Formula I and an electron donor material, can allow efficient transport of holes and electrons and superior power conversion efficiency by ensuring stability by controlling the aggregation of the first electron acceptor domain and optimizing blend morphology. Specifically, the first electron acceptor material, the second electron acceptor compound represented by Chemical Formula I and the electron donor material may be mixed to improve the performance of an organic photovoltaic device including the same.

The first electron acceptor material and the second electron acceptor compound may be mixed at 50-150 parts by weight and 1-50 parts by weight, respectively, specifically at 70-130 parts by weight and 5-40 parts by weight, respectively, more specifically at 80-120 parts by weight and 10-30 parts by weight, respectively, further more specifically at 90-110 parts by weight and 15-25 parts by weight, respectively, most specifically at 100-110 parts by weight and 17-22 parts by weight, respectively, based on 100 parts by weight of the electron donor material.

Chemical Formula I may be one or more selected from Chemical Formulas Ia to Ic. Specifically, superior performance may be maintained even at high temperatures of 80° C. or above when Chemical Formula I is one or more selected from Chemical Formulas Ia to Ic. Most specifically, Chemical Formula I may be Chemical Formula Ia. When a second electron acceptor polymer represented by Chemical Formula Ia is used, charge generation in the photoactive layer may be improved as the aggregation of the first electron acceptor domain is prevented and stable and uniform morphology is achieved. In addition, the performance of the organic solar cell may be improved significantly as charge transport is induced effectively.

[Chemical Formula Ia]

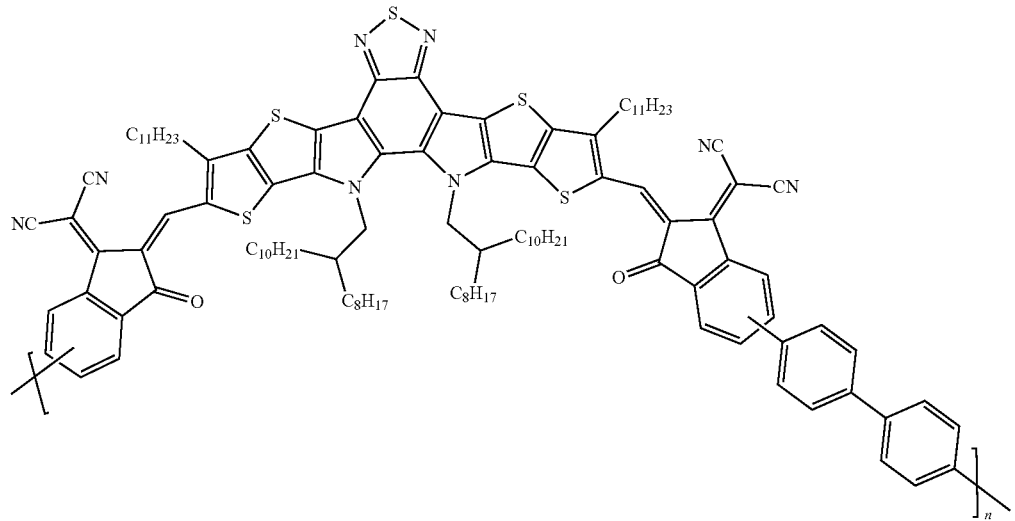

[Chemical Formula Ib]

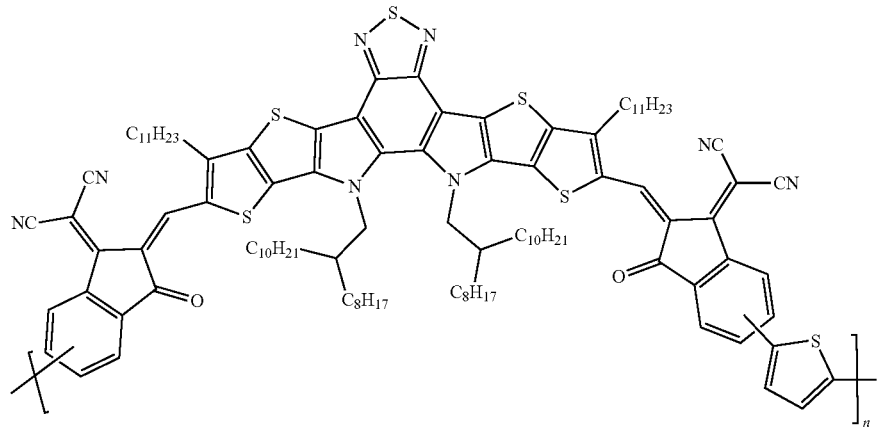

[Chemical Formula Ic]

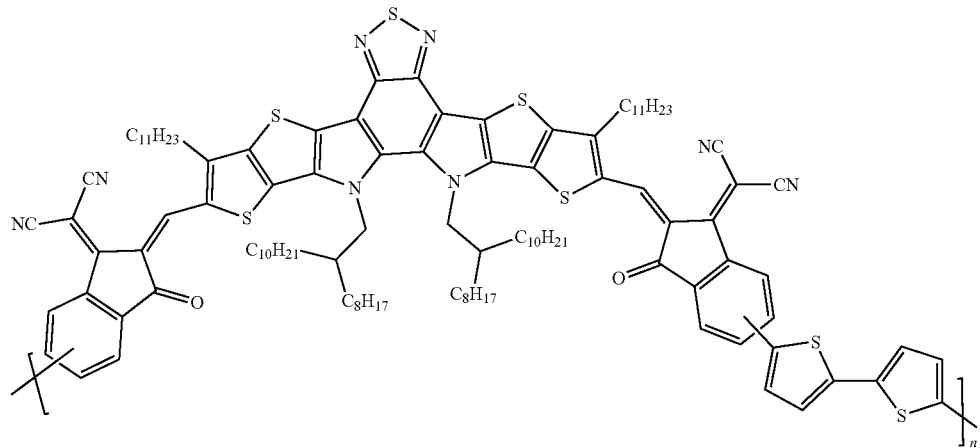

In Chemical Formulas Ia to Ic, n is an integer in a range from 1 to 1000.

In addition, the material represented by Chemical Formula 1 may specifically have a number-average molecular weight ($M_n$) of 2-50 kDa. Within this range, the performance of the photoactive layer may be improved remarkably without decreased power conversion efficiency. More specifically, the material represented by Chemical Formula 1 has a number-average molecular weight ($M_n$) of 5-20 kDa, more specifically 5-15 kDa, most specifically 6-15 kDa.

The first electron acceptor material may be any existing electron acceptor material without special limitation. Specifically, it may be one or more selected from a group consisting of fullerene, 6,6-phenyl-C61-butyric acid methyl ester (PCBM(C61)), PCBM(C60), PCBM(C70), PCBM (C71), PCBM(C76), PCBM(C80), PCBM(C82), indene-$C_{60}$ bisadduct (ICBA), 6,6-phenyl-C61-butyric acid cholesteryl ester (PCBCR), polybenzimidazole, perylene, poly[[N,N'-bis(2-octyldodecyl)-napthalene-1,4,5,8-bis(dicarboximide)-2,6-diyl]-alt-5,5'-(2,2'-bithiophene)] (NDI2OD-T2), naphthalene diimide (NDI)-selenophene copolymer (PNDIS-HD), poly[(E)-2,7-bis(2-decyltetradecyl)-4-methyl-9-(5-(2-(5-methylthiophen-2-yl)vinyl)thiophen-2-yl)benzo[lmn][3,8]phenanthroline-1,3,6,8(2H,7H)-tetraone] (PNDI-TVT), poly[[N,N'-bis(2-hexyldecyl)naphthalene1,4,5,8-bis(dicarboximide)-2,6-diyl]-alt-5,5'-thiophene] (PNDI2HD-T), 3,9-bis(2-methylene-(3-(1,1-dicyanomethylene)-indanone))-5,5,11,11-tetrakis(4-hexylphenyl)-dithieno[2,3-d:2',3'-d']-s-indaceno[1,2-b:5,6-b']dithiophene (ITIC), 3,9-bis(2-methylene-(3-(1,1-dicyanomethylene)-indanone))-5,5,11,11-tetrakis(5-hexylthienyl)-dithieno[2,3-d:2',3'-d']-s-indaceno[1,2-b:5,6-b']dithiophene (ITIC-Th), 2,7-bis(3-dicyanomethylene-2Z-methylene-indan-1-one)-4,4,9,9-tetrahexyl-4,9-dihydro-s-indaceno[1,2-b:5,6-b']dithiophene (IDIC), 3,9-bis(2-methylene-((3-(1,1-dicyanomethylene)-6,7-difluoro)-indanone))-5,5,11,11-tetrakis(4-hexylphenyl)-dithieno[2,3-d:2',3'-d']-s-indaceno[1,2-b:5,6-b']dithiophene (ITIC-4F), 2,2'-((2Z,2'Z)-(((4,4,9-tris(4-hexylphenyl)-9-(4-pentylphenyl)-4,9-dihydro-s-indaceno[1,2-b:5,6-b-dithiophene-2,7-diyl)bis(4-((2-ethylhexyl)oxy)thiophene-5,2-diyl))bis(methanylidene))bis(5,6-difluoro-3-oxo-2,3-dihydro-1H-indene-2,1-diylidene))dimalononitrile (IEICO-4F), 2,2'-((2Z,2'Z)-(((4,4,9-tris(4-hexylphenyl)-9-(4-pentylphenyl)-4,9-dihydro-s-indaceno[1,2-b:5,6-b-dithiophene-2,7-diyl)bis(4-((2-ethylhexyl)oxy)thiophene-5,2-diyl))bis(methanylidene))bis(5,6-dichloro-3-oxo-2,3-dihydro-1H-indene-2,1-diylidene))dimalononitrile (IEICO-4Cl), 2,2'-((2Z,2'Z)-((12,13-bis(2-ethylhexyl)-3,9-diundecyl-12,13-dihydro-[1,2,5]thiadiazolo[3,4-e]thieno[2'',3'':4',5']thieno[2',3':4,5]pyrrolo[3,2-g]thieno[2',3':4,5]thieno[3,2-b]indole-2,10-diyl)bis(methanylidene))bis(5,6-difluoro-3-oxo-2,3-dihydro-1H-indene-2,1-diylidene)) dimalononitrile (Y6 or BTP-4F), 2,2'-((2Z,2'Z)-((12,13-bis (2-ethylhexyl)-3,9-diundecyl-12,13-dihydro-[1,2,5] thiadiazolo[3,4-e]thieno[2'',3'':4',5']thieno[2',3':4,5]pyrrole [3,2-g]thieno[2',3':4,5]thieno[3,2-b]indole-2,10-diyl)bis (methanylidene))bis(5,6-dichloro-3-oxo-2,3-dihydro-1H-indene-2,1-diylidene))dimalononitrile (Y7 or BTP-4C1) and N3, more specifically Y6-N3. In the present disclosure, Y6-N3 is a non-fullerene-based electron acceptor molecule sold by 1-Material Inc. (common name: Y6N3 or Y6-N3, Cat. No: N3) and may be represented by Chemical Formula A. Y6-N3 is also called 2,2'-((2Z,2'Z)-((12,13-bis(3-ethylheptyl)-3,9-diundecyl-12,13-dihydro-[1,2,5]thiadiazolo[3,4-e]thieno[2'',3'':4',5']thieno[2',3':4,5]pyrrolo[3,2-g]thieno[2',3':4,5]thieno[3,2-b]indole-2,10-diyl)bis(methanylylidene))bis(5,6-difluoro-3-oxo-2,3-dihydro-1H-indene-2,1-diylidene))dimalononitrile.

[Chemical Formula A]

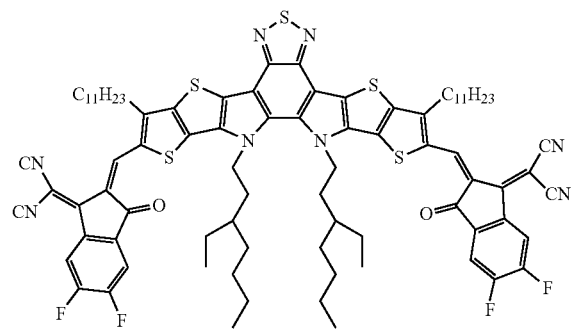

The electron donor material is not specially limited as long as it is a common electron donor material. Specifically, it may be one or more selected from a group consisting of poly[[4,8-bis[(2-ethylhexyl)oxy]benzo[1,2-b:4,5-b']dithiophene-2,6-diyl][3-fluoro-2-[(2-eth ylhexyl)carbonyl]thieno [3,4-b]thiophenediyl]] (PTB7), poly[3,6-bis(5-thiophen-2-yl)-2,5-bis(2-octyldodecyl)pyrrolo[3,4-c]pyrrole-1,4(2H,5H)-dione-2,2'-diyl-alt-thieno[3,2-b]thiophen2,5-diyl] (PDPP2T-TT), poly(3-octylthiophene-2,5-diyl)(P3OT), poly (p-phenylene vinylene) (PPV), poly(dioctyl fluorene), poly [2-methoxy-5-(2-ethylhexyloxy)-1,4-phenylenevinylene] (MEHPPV), poly[2-methoxy-5-(3',7''-dimethyloctyloxy)-1, 4-phenylenevinylene] (MDMO-PPV), poly[2,6-(4,4-bis-(2-ethylhexyl)-4H-cyclopenta [2,1-b;3,4-b']dithiophene)-alt-4, 7(2,1,3-benzothiadiazole)] (PCPDTBT), poly[4,8-bis(5-(2-ethylhexyl)thiophen-2-yl)-benzo[1,2-b:4,5-b']dithiophene-alt-5-octyl-4H-thieno[3,4-6-c]pyrrole-4,6(5H)-dione] (PBDTTTPD), poly[(2,5-bis(2-hexyldecyloxy)phenylene)-alt-(5,6-difluoro-4,7-di(thiophen-2-yl)benzo-[c][1,2,5]thiadiazole)] (PPDT2FBT), poly(3-hexylthiophene)(P3HT), poly{1-(5-(4,8-bis(5-(2-ethylhexyl)thiophen-2-yl)-6-methylbenzo[1,2-b:4,5-b']-dithiophen-2-yl)thiophen-2-yl)-5,7-bis(2-ethylhexyl)-3-(5-methylthiophen-2-yl)benzo-[1,2-c:4, 5-c'' ]dithiophene-4,8-dione} (PBDTBDDT) and poly[(2,6-(4,8-bis(5-(2-ethylhexyl-3-fluoro)thiophen-2-yl)-benzo[1,2-b:4,5-b']dithiophene))-alt-(5,5-(1',3'-di-2-thienyl-5',7'-bis(2-ethylhexyl)benzo[1',2'-c:4',5'-c']dithiophene-4,8-dione)] (PBDB-TF, PM6), more specifically PBDB-TF, PM6 (poly [(2,6-(4,8-bis(5-(2-ethylhexyl-3-fluoro)thiophen-2-yl)-benzo[1,2-b:4,5-b']dithiophene))-alt-(5,5-(1',3'-di-2-thienyl-5',7'-bis(2-ethylhexyl)benzo[1',2'-c:4',5'-c']dithiophene-4, 8-di one)]].

The ternary photoactive layer composition may further contain one or more selected from a group consisting of chlorobenzene, chloroform, p-xylene, 1,2-dichlorobenzene, trichlorobenzene, toluene, chloronaphthalene and 1,8-diiodooctane as a solvent. Specifically, it may contain a mixture solvent of chloroform and 1-chloronaphthalene.

The solvent may be a mixture of chloroform and 1-chloronaphthalene at a volume ratio of 0.995:0.001-0.01, specifically 0.995:0.001-0.009, 0.995:0.002-0.007, 0.995: 0.003-0.006 or 0.995:0.004-0.005.

In another aspect, the present disclosure relates to an organic solar cell including: a first electrode; an electron transport layer formed on the first electrode; a photoactive layer including the ternary photoactive layer composition described above and formed on the electron transport layer; a hole transport layer formed on the photoactive layer; and a second electrode formed on the hole transport layer.

The organic solar cell according to the present disclosure, which includes a ternary mixture including the first electron acceptor material, the second electron acceptor compound represented by Chemical Formula I and the electron donor material described above in the photoactive layer, exhibits superior power conversion efficiency even with a small area and also exhibits high efficiency and stabilized morphology for a large area by solving various problems occurring during area enlargement.

The first electrode may be one or more selected from a group consisting of indium tin oxide (ITO), fluorine tin oxide (FTO), silver (Ag) nanowire and silver nanomesh, more specifically ITO.

The electron transport layer may be one or more selected from a group consisting of ZnO, LiF, $TiO_x$, $TiO_2$, $CsCO_3$ and Ca, and the electron transport layer may be used to improve electron transport from the photoactive layer to the first electrode. The electron transport layer may be formed through spin coating, etc.

The photoactive layer is a bulk hetero junction structure wherein the first electron acceptor material, the second electron acceptor compound and the electron donor material are mixed and may provide photovoltaic effect through very fast charge transport and separation between the first electron acceptor material, the second electron acceptor compound and the electron donor material.

A detailed description about the first electron acceptor material, the second electron acceptor compound and the electron donor material constituting the photoactive layer will be omitted because they were described above with regard to the ternary photoactive layer composition.

The photoactive layer may exhibit remarkably superior performance by controlling the morphology of the photoactive layer during area enlargement as the excessive crystal growth and aggregation of the first electron acceptor material are prevented. In addition, more charges may be generated and transported easily since the lifetime of excitons in the electron acceptor domain is improved.

The ternary photoactive layer composition according to the present disclosure may be prepared into a photoactive layer by coating through a large-area process. The photoactive layer of the present disclosure has improved power conversion efficiency due to superiorly controlled morphology of the photoactive layer as compared to the existing photoactive layers. Accordingly, the photoactive layer exhibits superior efficiency of 15% higher even in a room-temperature process including printing, spin coating, screen printing, doctor blade method and shadow mask method.

The hole transport layer may include one or more selected from a group consisting of molybdenum oxide ($MoO_2$, $MoO_3$), PEDOT:PSS (poly(3,4-ethylenedioxythiophene) polystyrene sulfonate), tungsten oxide ($WO_3$), nickel oxide and cerium-doped tungsten oxide ($CeWO_3$).

The second electrode may include one or more selected from a group consisting of Au, Fe, Ag, Cu, Cr, W, Al, Mo, Zn, Ni, Pt, Pd, Co, In, Mn, Si, Ta, Ti, Sn, Pb, V, Ru, Ir, Zr, Rh, $MoO_3$ and Mg, specifically silver or silver/molybdenum oxide ($MoO_3$).

In an exemplary embodiment of the present disclosure, the organic solar cell may be used in various applications, including installation in houses, buildings, vehicles, ships, roadside guardrails, soundproofing walls, etc., although not being limited thereto.

Hereinafter, the present disclosure is described more specifically through examples. However, the examples are provided only for illustrative purposes and the scope of the present disclosure is not limited by them.

Synthesis Example 1: Preparation of Compound Represented by Chemical Formula 3

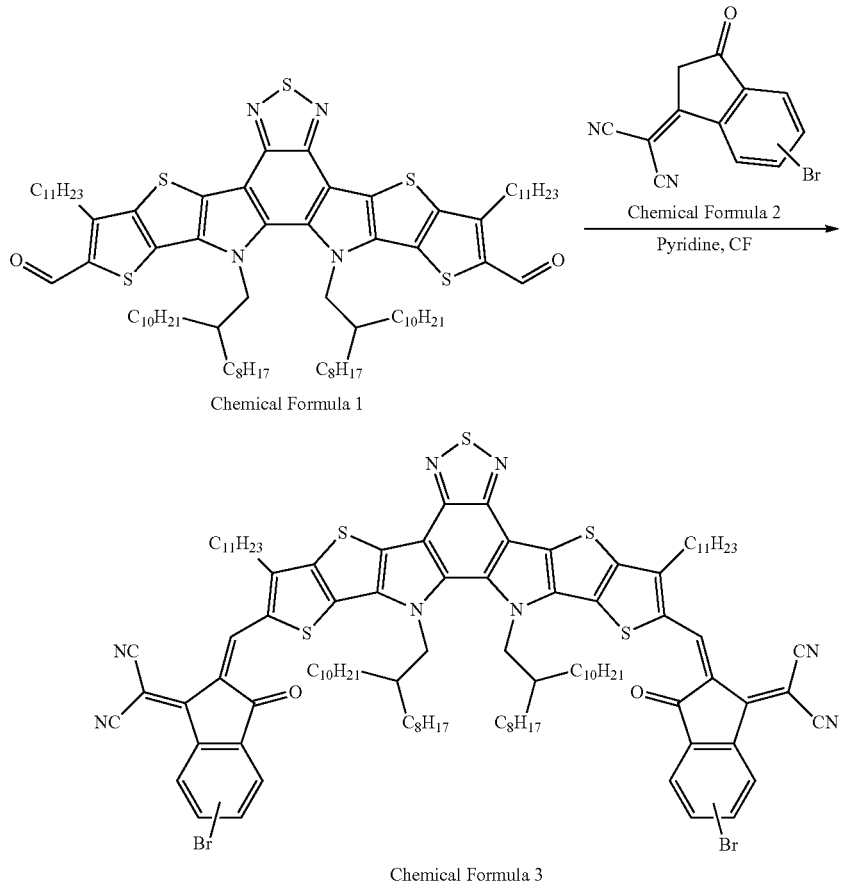

A compound represented by Chemical Formula 3 (2,2'-((2Z,2'Z)-((12,13-bis(2-octyldodecyl)-3,9-diundecyl-12,13-dihydro-[1,2,5]thiadiazolo[3,4-e]thieno[2'',3'':4',5']thieno[2',3':4,5]pyrrolo[3,2-g]thieno[2',3':4,5]thieno[3,2-b]indole-2,10-diyl)bis(methaneylylidene))bis((5)6-bromo-3-oxo-2,3-dihydro-1H-indene-2,1-diyliden e))dimalononitrile) was prepared according to Reaction Scheme 1. Details are as follows.

After dissolving 12,13-bis(2-octyldodecyl)-3,9-diundecyl-12,13-dihydro-[1,2,5]thiadiazolo[3,4-e]thieno[2'',3'':4',5']thieno[2',3':4,5]pyrrolo[3,2-g]thieno[2',3':4,5]thieno[3,2-b]indole-2,10-dicarbaldehyde (Chemical Formula 1; 0.5 g, 0.367 mmol) and 2-((5)6-bromo-3-oxo-2,3-dihydro-1H-inden-1-ylidene)malononitrile (Chemical Formula 2; 0.4 g, 1.47 mmol) in chloroform (40 mL) and then adding pyridine (1.3 mL), the mixture was refluxed for 12 hours while heating at 65° C. After removing the solvent from the refluxed solution and adding dichloromethane and water to the residue, the mixture was stirred and then layer separation was induced using a separatory funnel. After separating the organic layer and drying with anhydrous $MgSO_4$, 0.63 g of the compound represented by Chemical Formula 3 was obtained with a yield of 90% by purifying through silica gel column chromatography (DCM:Hex=1:1).

$^1$H NMR ($CDCl_3$), δ (ppm): 9.16 (s, 2H), 8.85 (d, 1.5H), 8.57 (d, 0.5H), 8.06 (d, 0.5H), 7.90 (d, 0.5H), 7.88 (d, 1.5H), 7.86 (d, 0.5H), 7.82 (d, 1.5H), 4.80 (4H), 3.24 (4H) 2.16 (2H), 1.9 (4H) 1.52 (3H), 1.37 (3H), 1.3 (m, 24H) 1.21-1.13 (m, 27H) 1.02 (m, 36H) 0.88-0.76 (tt, 24H).

Synthesis Example 2: Synthesis of Compound Represented by Chemical Formula 5

[Reaction Scheme 2]

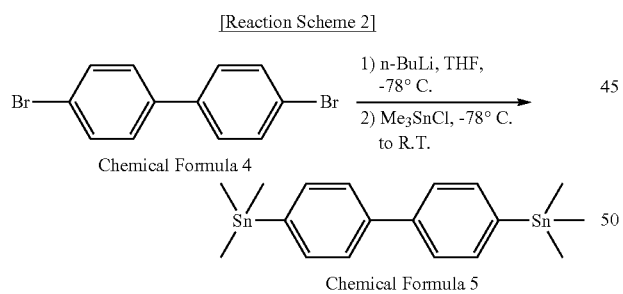

Chemical Formula 4

Chemical Formula 5

A compound represented by Chemical Formula 5 (4,4'-bis(trimethylstannyl)-1,1'-biphenyl) was prepared according to Reaction Scheme 2. Details are as follows.

4,4'-Dibromo-1,1'-biphenyl (Chemical Formula 4; 0.4 g, 3.05 mmol) was dissolved in anhydrous THF (12 mL) and then cooled to −78° C. under argon atmosphere. After slowly adding n-BuLi (1.6 mL, 1.6 M, 6.72 mmol) and conducting reaction at −78° C. for 1 hour, reaction was conducted for 1 hour while heating to room temperature. Then, after cooling again to −78° C. and adding a trimethyltin chloride solution ($SnMe_3Cl$, 1 M, 7.63 mL, 7.63 mmol), reaction was conducted at room temperature for 12 hours. After stopping reaction by adding water, the reaction product was extracted with diethyl ether. After removing the solvent, 0.44 g of the compound represented by Chemical Formula 5 (yield: 57%) was obtained by recrystallizing in acetonitrile.

$^1$H NMR ($CDCl_3$), δ (ppm): 7.56 (d, 8H), 0.38-0.24 (s, 18H).

Synthesis Example 3: Synthesis of Compound Represented by Chemical Formula 7

[Reaction Scheme 3]

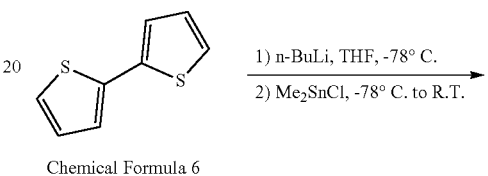

Chemical Formula 6

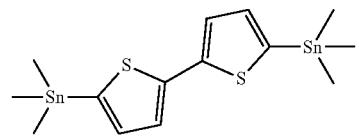

Chemical Formula 7

A compound represented by Chemical Formula 7 (5,5'-bis(trimethylstannyl)-2,2'-bithiophene) was prepared according to Reaction Scheme 3. Details are as follows.

2,2'-Bithiophene (Chemical Formula 6; 2.0 g, 12.03 mmol) was dissolved in anhydrous THF (60 mL) and cooled to −78° C. under argon atmosphere. After slowly adding n-BuLi (15.8 mL, 1.6 M, 25.26 mmol) and conducting reaction at −78° C. for 1 hour, reaction was conducted further for 1 hour while heating to room temperature. After cooling again to −78° C. and adding a trimethyltin chloride solution ($SnMe_3Cl$, 1 M, 26.46 mL, 26.46 mmol), reaction was conducted at room temperature for 24 hours. After stopping the reaction by adding water, the reaction product was extracted with diethyl ether. After removing the solvent, 3.8 g of the compound represented by Chemical Formula 7 (yield: 64.2%) was obtained by recrystallizing in IPA (isopropyl alcohol).

$^1$H NMR ($CDCl_3$), δ (ppm): 7.27 (d, 2H), 7.08 (d, 2H), 0.19-0.56 (s, 18H).

Preparation Example 1. Synthesis of PY-P2 (Chemical Formula 10) Polymer Compound

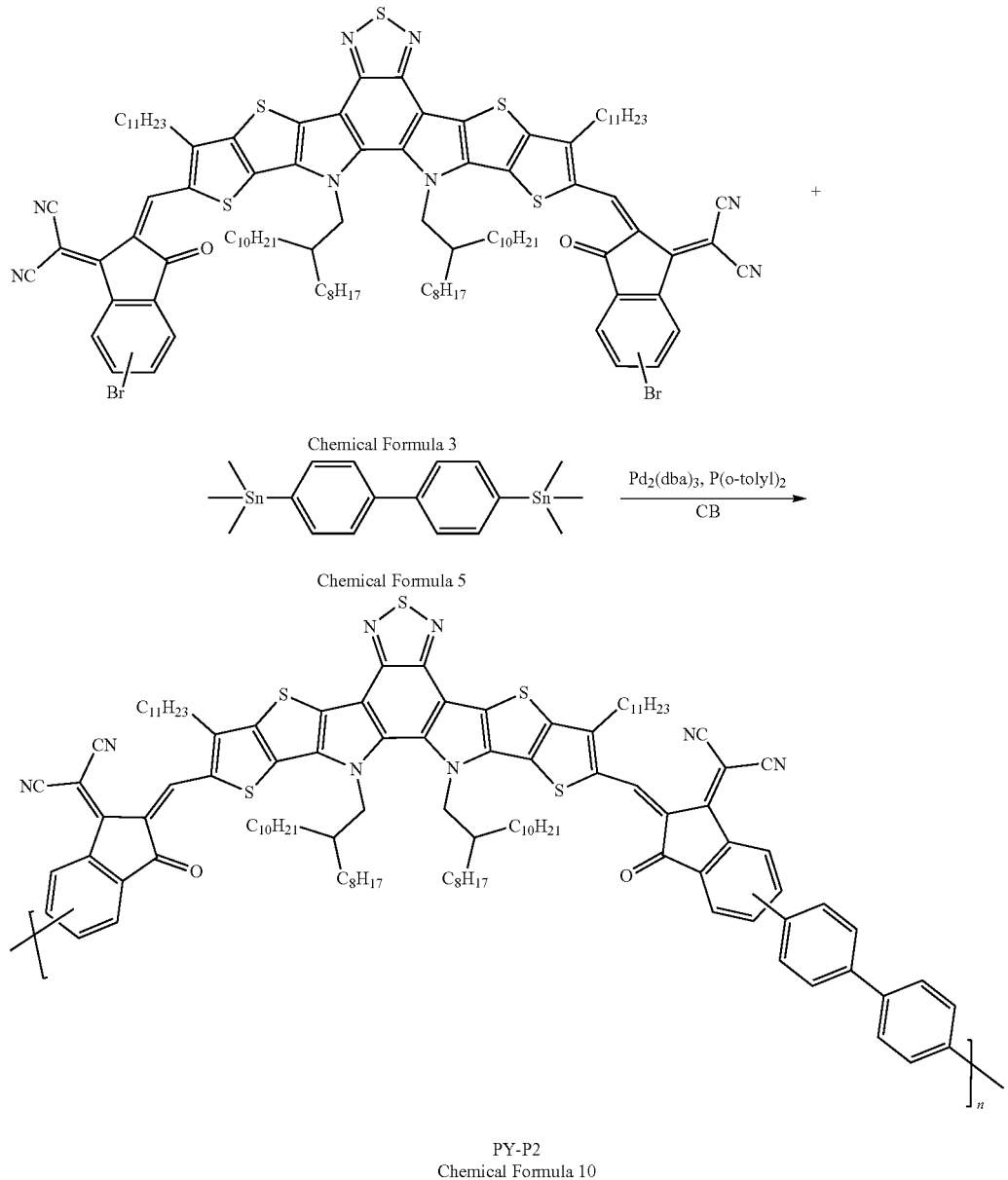

[Reaction Scheme 4]

Chemical Formula 3

Chemical Formula 5

PY-P2
Chemical Formula 10

A PY-P2 polymer compound represented by Chemical Formula 10 was prepared according to Reaction Scheme 4. Details are as follows.

2,2'-((2Z,2'Z)-((12,13-Bis(2-octyldodecyl)-3,9-diundecyl-12,13-dihydro-[1,2,5]thia diazolo[3,4-e]thieno[2'',3''':4',5']thieno[2',3':4,5]pyrrolo[3,2-g]thieno[2',3':4,5]thieno[3,2-b]indole-2,10-diyl)bis(methaneylylidene))bis((5)6-bromo-3-oxo-2,3-dihydro-1H-indene-2,1-diylidene))dimalononitrile (Chemical Formula 3; 100 mg, 0.0534 mmol), 4,4'-bis(trimethylstannyl)-1,1'-biphenyl (Chemical Formula 5; 25.62 mg, 0.0534 mmol), tris(dibenzylideneacetone)dipalladium(0) (Pd$_2$(dba)$_3$) (2.44 mg, 2.67 μmol) and tri(o-tolyl)phosphine (P(o-tolyl)$_3$) (3.25 mg, 10.7 μmol) were added to a reaction flask and dissolved by adding degassed chlorobenzene (CB, 2.0 mL). After purging with argon for 20 minutes, reaction was conducted at 120° C. for 48 hours. After the reaction was completed, the reaction solution was diluted by adding chlorobenzene and a precipitate was formed by adding acetone. Then, the precipitate was filtered through a thimble filter and Soxhlet-purified sequentially with methanol, hexane, ethyl acetate, chloroform and chlorobenzene. The purified solution was concentrated, re-precipitated with acetone and then filtered to obtain 66.1 mg of the PY-P2 (Chemical Formula 10) polymer compound (yield: 65.3%).

$M_n$=6.84 kDa, PDI=1.36.

Preparation Example 2. Synthesis of PY-T1 (Chemical Formula 9) Polymer Compound

[Reaction Scheme 5]

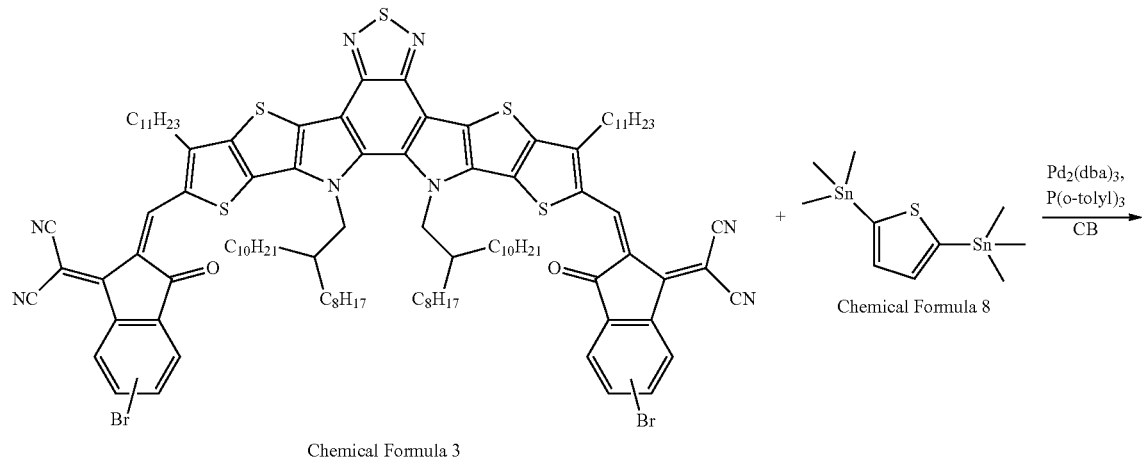

Chemical Formula 3

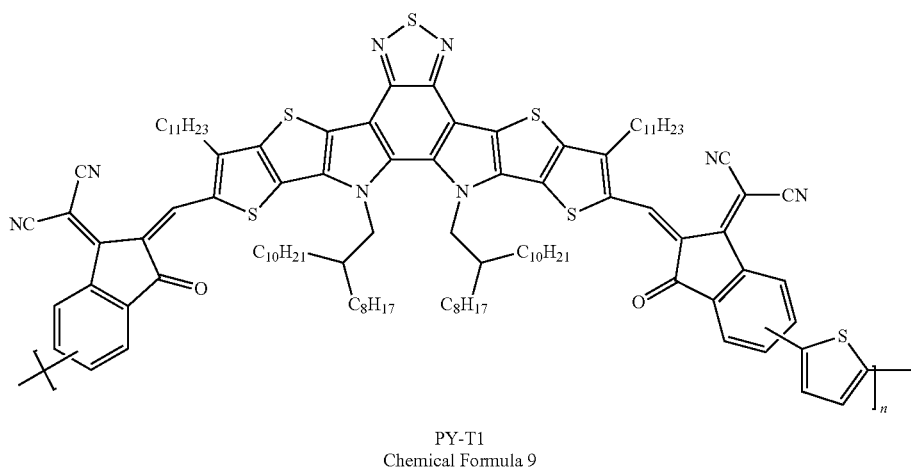

PY-T1
Chemical Formula 9

A PY-T1 polymer compound represented by Chemical Formula 9 was prepared according to Reaction Scheme 5. Details are as follows.

2,2'-((2Z,2'Z)-((12,13-Bis(2-octyldodecyl)-3,9-diundecyl-12,13-dihydro-[1,2,5]thia diazolo[3,4-e]thieno[2",3"׃4',5']thieno[2',3'׃4,5]pyrrolo[3,2-g]thieno[2',3'׃4,5]thieno[3,2-b]indole-2,10-diyl)bis(methaneylylidene))bis((5)6-bromo-3-oxo-2,3-dihydro-1H-indene-2,1-diylidene))dimalononitrile (Chemical Formula 3; 100 mg, 0.0534 mmol), 2,5-bis(trimethylstannyl)thiophene (Chemical Formula 8; 31.9 mg, 0.0534 mmol), tris(dibenzylideneacetone)dipalladium(0) ($Pd_2(dba)_3$) (2.44 mg, 2.67 μmol) and tri(o-tolyl)phosphine (P(o-tolyl)$_3$) (3.25 mg, 10.7 μmol) were added to a reaction flask and dissolved by adding degassed chlorobenzene (CB, 2.0 mL). After purging with argon for 20 minutes, reaction was conducted at 120° C. for 48 hours. After the reaction was completed, the reaction solution was diluted by adding chlorobenzene and a precipitate was formed by adding acetone. Then, the precipitate was filtered through a thimble filter and Soxhlet-purified sequentially with methanol, hexane, ethyl acetate, chloroform and chlorobenzene. The purified solution was concentrated, re-precipitated with acetone and then filtered to obtain 71.7 mg of the PY-T1 (Chemical Formula 9) polymer compound (yield: 73.5%).

$M_n$=7.22 kDa, PDI=1.66.

Preparation Example 3. Synthesis of PY-T2 (Chemical Formula 11) Polymer Compound

[Reaction Scheme 6]

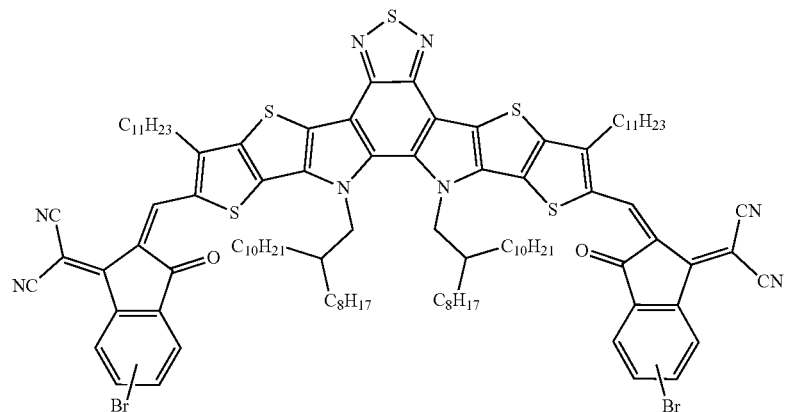

Chemical Formula 3

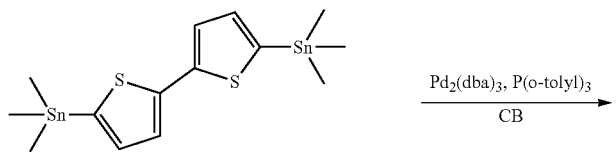

Chemical Formula 7

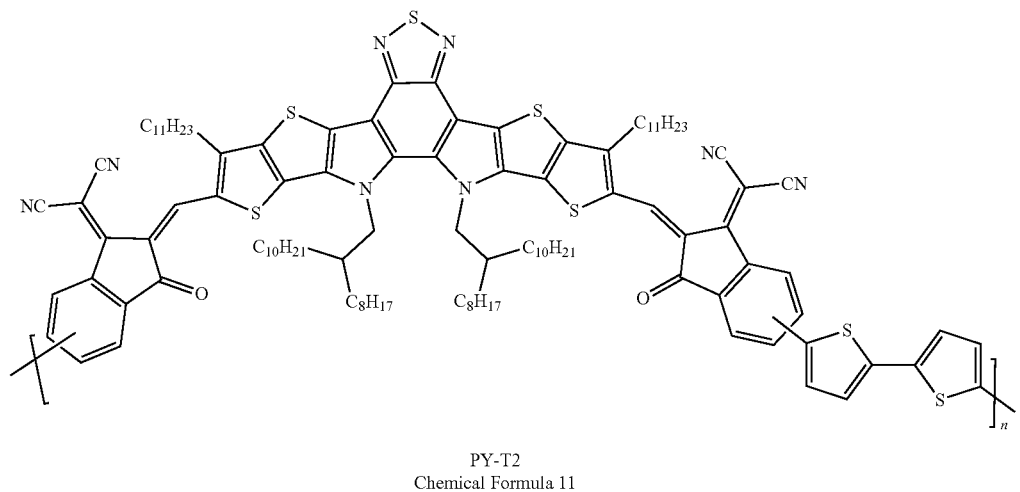

PY-T2
Chemical Formula 11

A PY-T2 polymer compound represented by Chemical Formula 11 was prepared according to Reaction Scheme 6. Details are as follows.

2,2'-((2Z,2'Z)-((12,13-Bis(2-octyldodecyl)-3,9-diundecyl-12,13-dihydro-[1,2,5]thia diazolo[3,4-e]thieno[2″,3‴:4',5']thieno[2',3':4,5]pyrrolo[3,2-g]thieno[2',3':4,5]thieno[3,2-b]indole-2,10-diyl)bis(methaneylylidene))bis((5)6-bromo-3-oxo-2,3-dihydro-1H-indene-2,1-diylidene)) dimalononitrile (Chemical Formula 3; 100 mg, 0.0534 mmol), 5,5'-bis(trimethylstannyl)-2,2'-bithiophene (Chemical Formula 7; 26.3 mg, 0.0534 mmol), tris(dibenzylideneacetone)dipalladium(0) (Pd$_2$(dba)$_3$) (2.44 mg, 2.67 μmol) and tri(o-tolyl)phosphine (P(o-tolyl)$_3$) (3.25 mg, 10.7 μmol) were added to a reaction flask and dissolved by adding degassed chlorobenzene (CB, 2.0 mL). After purging with argon for 20 minutes, reaction was conducted at 120° C. for 48 hours. After the reaction was completed, the reaction solution was diluted by adding chlorobenzene and a precipitate was formed by adding acetone. Then, the precipitate was filtered through a thimble filter and Soxhlet-purified sequentially with methanol, hexane, ethyl acetate, chloroform and chlorobenzene. The purified solution was concentrated, re-precipitated with acetone and then filtered to obtain 34.3 mg of the PY-T2 (Chemical Formula 11) polymer compound (yield: 33.6%).

$M_n$=7.19 kDa, PDI=1.46.

Example 1. Ternary Photoactive Layer Composition (PY-P2

As electron donor materials, PM6 (Mn: 24.2 kDa, Mw: 88.0 kDa, PDI: 3.361) was purchased form 1-Material Inc. and Y6-N3 was purchased form 1-Material Inc. (common name: Y6N3 N3, Cat. No: N3).

For preparation of a ternary photoactive layer composition for an organic solar cell, a mixture solution was prepared by mixing chloroform and 1-chloronaphthalene at a volume ratio of 0.995:0.005. After adding the PM6 (10 mg), N3 (10 mg) the PY-P2 (2 mg) polymer compound prepared in Preparation Example 1 to 1 mL of the mixture solution, a ternary photoactive layer composition was prepared by completely mixing the mixture by stirring at 50° C. for 5 hours.

Example 2. Ternary Photoactive Layer Composition (PY-T1)

A ternary photoactive layer composition was prepared in the same manner as in Example 1 except that the PY-T1 (2 mg) polymer compound prepared in Preparation Example 2 was used instead of the PY-P2 (2 mg) polymer compound prepared in Preparation Example 1.

Example 3. Ternary Photoactive Layer Composition (PY-T2)

A ternary photoactive layer composition was prepared in the same manner as in Example 1 except that the PY-T2 (2 mg) polymer compound prepared in Preparation Example 3 was used instead of the PY-P2 (2 mg) polymer compound prepared in Preparation Example 1.

Comparative Example 1. Binary Photoactive Layer Composition

A photoactive layer composition (binary blend) was prepared in the same manner as in Example 1 except that the PY-P2 (2 mg) polymer compound prepared in Preparation Example 1 was not added.

<Test Example 1> Performance of Organic Solar Cell

An indium tin oxide (ITO) substrate was ultrasonically washed in acetone for 10 minutes and then in isopropyl alcohol for 10 minutes and then dried. After spin-coating a zinc oxide (ZnO) solution on the dried indium tin oxide (ITO), the substrate was heat-treated at 200° C. for 30 minutes.

Next, one of the ternary photoactive layer compositions of Examples 1-3 was bar-coated (meniscus-coated) on the ZnO-coated ITO substrate at room temperature at a speed of 10 mm/s. Then, the coated sample was put in a vacuum chamber under a pressure of 105 Pa and then a hole transport layer and an upper electrode were deposited.

After depositing a molybdenum oxide ($MoO_3$) layer on the photoactive layer by thermal evaporation to a thickness of 3 nm using a shadow mask, a 1 $cm^2$-sized organic solar cell with a structure of ITO/ZnO/ternary photoactive layer/$MoO_3$/Ag was prepared by depositing a silver electrode to a thickness of 100 nm.

The organic solar cell prepared with the ternary photoactive layer composition of Example 1 was named as Experimental Example 1 (PM6:N3:PY-P2), the organic solar cell prepared with the ternary photoactive layer composition of Example 2 as Experimental Example 2 (PM6:N3:PY-T1), and the organic solar cell prepared with the ternary photoactive layer composition of Example 3 as Experimental Example 3 (PM6:N3:PY-T2).

As a control group, an organic solar cell was prepared in the same manner except that the photoactive layer composition of Comparative Example 1 wherein only the PM6 electron donor material and the N3 electron acceptor material were added was used instead of the ternary photoactive layer composition and it was named as Comparative Experimental Example 1 (PM6:N3).

The solar cell characteristics of the organic solar cell were analyzed using a Keithley 2400 digital source meter controlled by a computer under illumination of simulated AM 1.5 G solar light from an AM 1.5 solar simulator (Yamashita Denso, YSS-50A, with a single Xenon lamp). The AM 1.5 G light source (100 mW/$cm^2$) controlled using a PVM_1105 2×2 Si KG5 Window T-TC reference Si photodiode.

Figure 2:
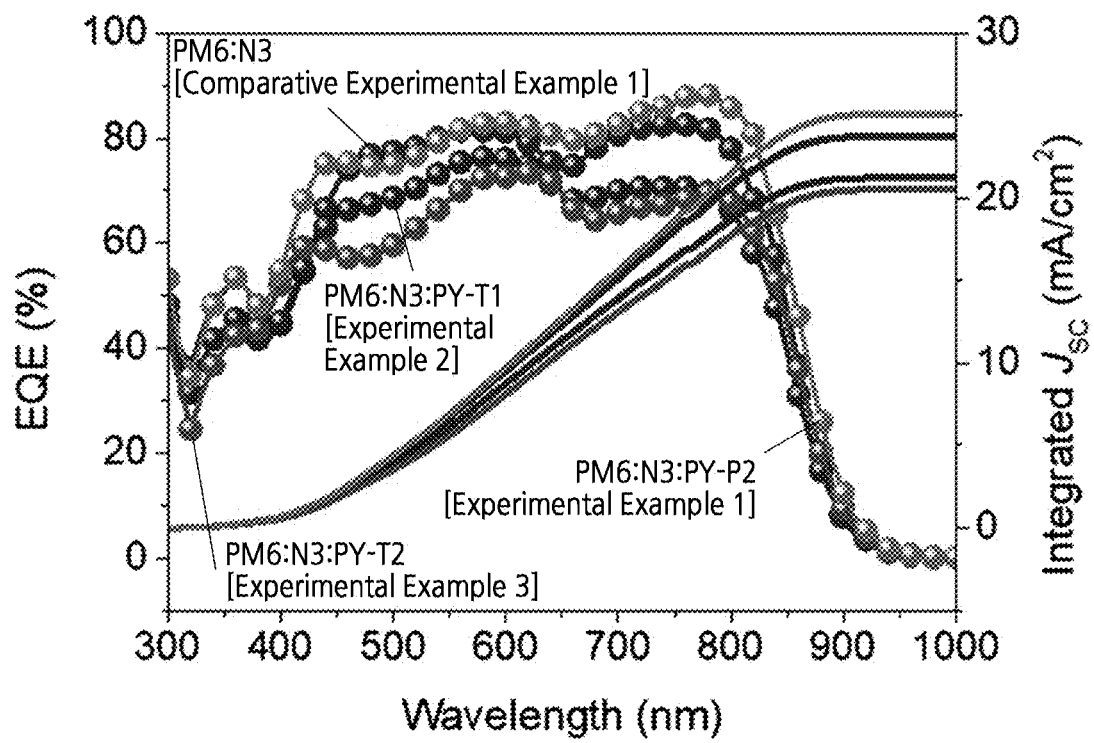
FIG. 2 shows a result of measuring the external quantum efficiency (EQE) of organic solar cells prepared in Experimental Examples 1-3 and Comparative Experimental Example 1.

FIG. 1 shows a result of measuring current density depending on voltage for the organic solar cells of Experimental Examples 1-3 and Comparative Experimental Example 1, and FIG. 2 shows a result of measuring the external quantum efficiency (EQE) of the organic solar cells prepared in Experimental Examples 1-3 and Comparative Experimental Example 1. The results are summarized in Table 1.

TABLE 1

| | Open-circuit voltage ($V_{oc}$, V) | Short-circuit current density ($J_{sc}$, mA/$cm^2$) | $J_{SC}^{cal}$ (mA/$cm^2$) | Fill factor (FF, %) | Power conversion efficiency (PCE, %) |
|---|---|---|---|---|---|
| PM6:N3 Comp. Experimental Ex. 1 | 0.837 (0.834 ± 0.004) | 23.89 (23.74 ± 0.32) | 23.77 | 64.23 (61.54 ± 1.59) | 12.87 (12.20 ± 0.36) |
| PM6:N3:PY-P2 Experimental Ex. 1 | 0.846 (0.843 ± 0.002) | 25.20 (25.08 ± 0.25) | 25.11 | 71.2 (69.81 ± 0.97) | 15.18 (14.76 ± 0.23) |
| PM6:N3:PY-T1 Experimental Ex. 2 | 0.859 (0.857 ± 0.002) | 22.69 (22.23 ± 0.51) | 21.24 | 63.42 (64.17 ± 0.67) | 12.36 (12.22 ± 0.17) |
| PM6:N3:PY-T2 Experimental Ex. 3 | 0.862 (0.852 ± 0.006) | 21.64 (21.42 ± 0.26) | 20.55 | 63.07 (60.90 ± 1.46) | 11.76 (11.12 ± 0.34) |

The result of measuring the performance of the organic solar cells prepared using the ternary photoactive layer compositions containing the second electron acceptor polymer compounds is shown in FIGS. 1 and 2 and Table 1. The performance of the large-area (1 cm$^2$) organic solar cell prepared by bar coating (meniscus coating) was compared with that of the large-area (1 cm$^2$) organic solar cell prepared by bar coating (meniscus coating) using the existing photoactive layer.

In general, the performance of organic solar cells is compared by preparing laboratory-scale small-area organic solar cells by spin coating. In this case, there is a limitation that many problems that may occur during a large-area roll-to-roll process cannot be identified. Accordingly, in the present disclosure, bar coating (meniscus coating) which is similar to the roll-to-roll process is used to identify the problems that may occur during area enlargement.

For Comparative Experimental Example 1, wherein the photoactive layer was prepared by bar coating (meniscus coating) for area enlargement, the power conversion efficiency of the organic solar cell was only 12-13% although PM6 and N3 were used as electron acceptor and electron donor. Despite the development of various electron donor or electron acceptor materials exhibiting superior performance, aggregation of the electron acceptor material could not be avoided when they are prepared by meniscus coating for area enlargement due to slow evaporation of the solvent. The aggregation of the electron acceptor material is a big obstacle to commercialization of the solar cell because charge generation is limited and, thus, the power conversion efficiency of the organic solar cell is decreased significantly as compared to the small-area organic solar cells prepared by spin coating.

The present disclosure is directed to providing a ternary photoactive layer composition using a second electron acceptor material, which is capable of exhibiting high efficiency and stable morphology even with large area through meniscus coating with controlled aggregation of the electron acceptor and the electron donor, thereby controlling the aggregation of the first electron acceptor domain and ensuring performance and stability by optimizing the blend morphology. These effects will be identified in the test examples described below.

The organic solar cells using the ternary photoactive layers prepared from the polymer compounds of Example 2 and Example 3 (PY-T1, PY-T2) showed comparable power conversion efficiency despite the further addition of the second electron acceptor compound in addition to the first electron acceptor material and the electron donor material. That is to say, it was confirmed that the morphological stability of the photoactive layer can be ensured without affecting the performance of the photoactive layer (From the thermal stability described below, it could be confirmed that the morphological stability is maintained by preventing thermal change of the first electron acceptor.).

In contrast, the organic solar cell using the ternary photoactive layer to which the polymer compound (PY-P2) of Example 1 was added as the second electron acceptor (Experimental Example 1) showed a short-circuit current density of 25.20 mA/cm$^2$, a significantly increased fill factor of 71.20% and a significantly increased power conversion efficiency (PCE) of 15% or higher despite the area enlargement.

That is to say, the existing electron acceptor (first electron acceptor material) has the problem that aggregation may occur during large-area coating by meniscus coating due to low morphological stability or performance may be decreased with time or due to external factors (heat) even when the aggregation does not occur immediately. The ternary photoactive layer compositions using the polymer compounds of Examples 1-3 as the second electron acceptor polymer were presented to solve this problem and it was confirmed that the polymer compounds of Examples 1-3 can induce stable morphology without affecting the performance of the first electron acceptor and the electron donor.

In particular, it was confirmed that the polymer compound of Example 1 (PY-P2) prevents the aggregation of the first electron acceptor domain, improves charge generation in the photoactive layer through improved morphological stability and significantly increases the performance of the organic solar cell by effectively inducing charge transport.

Therefore, for preparation of an organic solar cell capable of stably maintaining morphology, it is preferred to use the ternary photoactive layer compositions containing the polymer compounds of Examples 1-3 as the second electron acceptor material, and it is the most preferred to use the ternary photoactive layer composition containing the polymer compound of Example 1 as the second electron acceptor material. In particular, if the polymer compounds of Examples 1-3 are used as the electron acceptor alone, the morphology characteristics of the organic solar cell may be worse than that of Comparative Experimental Example 1.

As shown in FIG. 2, it was confirmed that the organic solar cell using the ternary photoactive layer containing the polymer compound of Example 1 (PY-P2) has significantly improved ability of generating charges in the photoactive layer.

Figure 3:
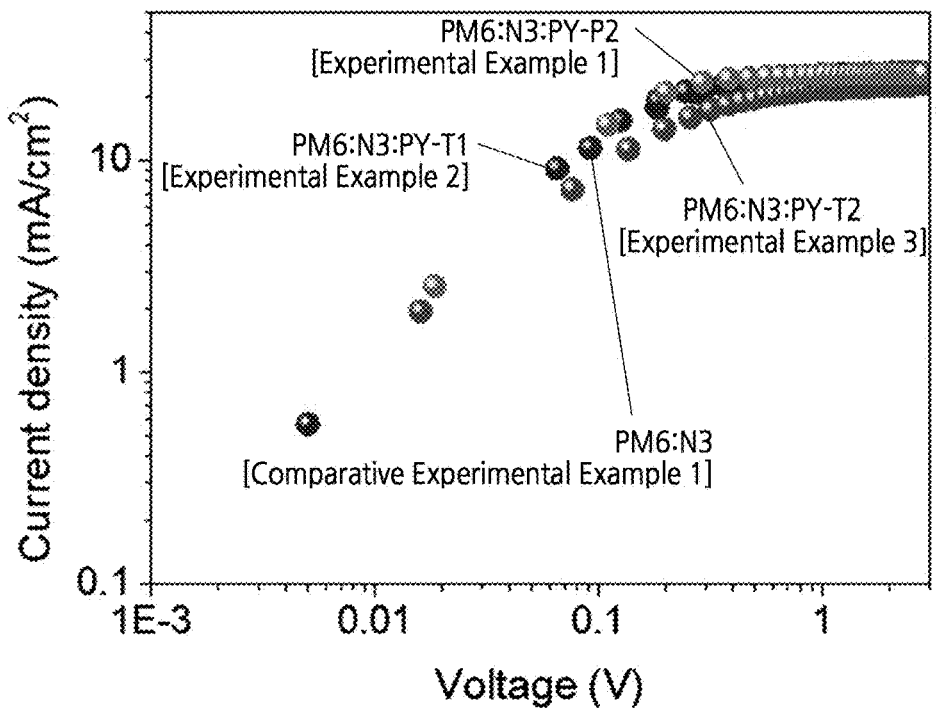
FIG. 3 shows a result of measuring the degree of charge separation for organic solar cells of Experimental Examples 1-3 and Comparative Experimental Example 1.

FIG. 3 shows a result of measuring the degree of charge separation of the organic solar cells of Experimental Examples 1-3 and Comparative Experimental Example 1. The result is summarized in Table 2.

TABLE 2

| | $J_{sat}$ (mA/cm$^2$) | $J_{ph}$* (mA/cm$^2$) | P (E,T) (%) | $G_{max}$ |
|---|---|---|---|---|
| PM6:N3 Comp. Experimental Ex. 1 | 26.09 | 24.96 | 95.6 | 1.09 × 10$^{28}$ |
| PM6:N3:PY-P2 Experimental Ex. 1 | 25.71 | 25.42 | 98.8 | 1.23 × 10$^{28}$ |
| PM6:N3:PY-T1 Experimental Ex. 2 | 24.29 | 23.14 | 95.2 | 1.01 × 10$^{28}$ |
| PM6:N3:PY-T2 Experimental Ex. 3 | 23.98 | 22.43 | 93.5 | 9.98 × 10$^{27}$ |

In order to investigate the degree of charge separation of the organic solar cells wherein the ternary photoactive layer compositions containing the polymer compounds prepared in Examples 1-3 were used, photo current density ($J_{ph}$) was measured in a bias voltage range from −10 to 2 V. The $J_{ph}$ curve could be obtained from the difference in the current density under illumination (100 mW cm$^{-2}$) and the current density in the dark, and the effective voltage $V_{eff}$ was calculated by subtracting $V_a$ from $V_0$ (where $V_0$ indicates the voltage at $J_{ph}$=0 and $V_a$ indicates the applied voltage). When $V_{eff}$ was high (10 V), transition and recombination were decreased greatly, almost all excitons were separated and charge carriers were collected at the electrode. FIG. 3 shows the result of measuring the $J_{ph}$-$V_{eff}$ characteristics of the organic solar cells of Experimental Examples 1-3 and Comparative Experimental Example 1. It was confirmed that the organic solar cells of Experimental Examples 2 and 3 wherein the second electron acceptor polymers of Examples 2 and 3 were used maintained performance similarly to that of Comparative Experimental Example 1.

It was confirmed that the organic solar cell of Experimental Example 1 wherein the polymer compound prepared in Example 1 (PY-P2) was used as the second electron acceptor material shows significantly increased charge separation efficiency as compared to Comparative Experimental Example 1. That is to say, it was confirmed that the second electron acceptor polymer compound of Example 1 (PY-P2) is mixed well with the first electron acceptor material, thereby increasing the lifetime of excitons and allowing effective charge separation as the electron acceptor is interposed between the electron donor material, resulting in significant improvement in short-circuit current density ($J_{sc}$).

Figure 4:
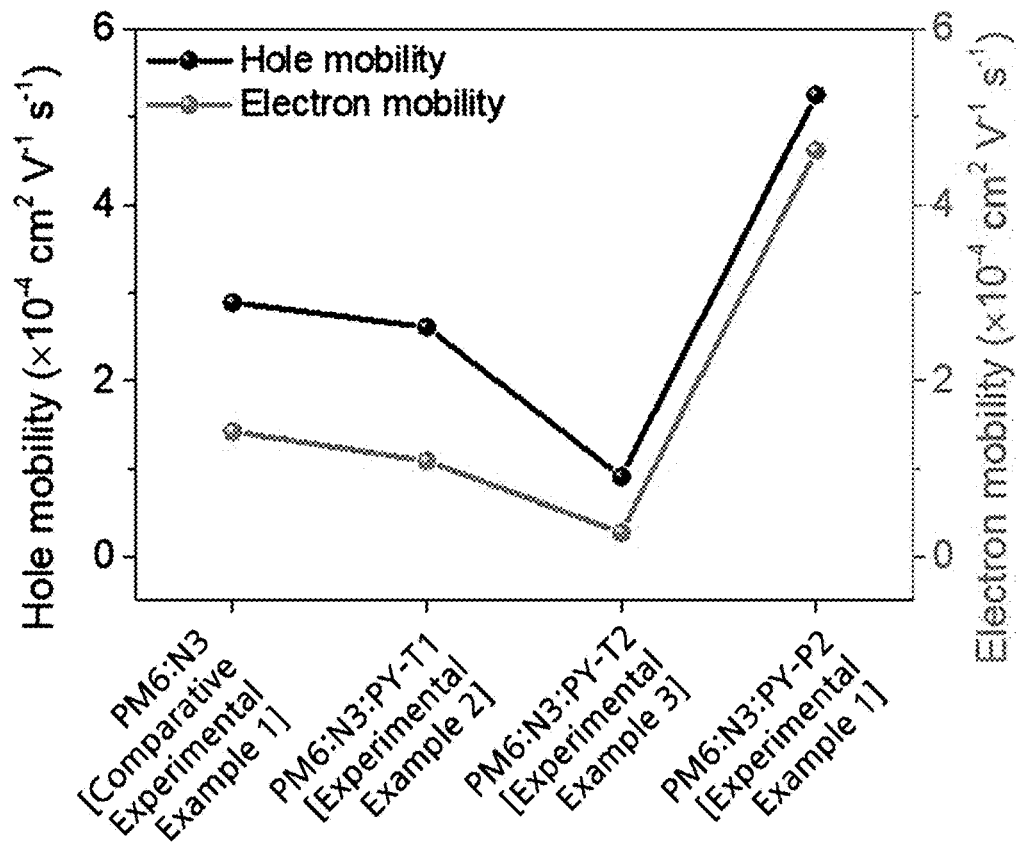
FIG. 4 shows a result of measuring the hole and electron mobility of organic solar cells of Experimental Examples 1-3 and Comparative Experimental Example 1.

FIG. 4 shows a result of measuring the hole and electron mobility of the photoactive layer for the organic solar cells of Experimental Examples 1-3 and Comparative Experimental Example 1. The result is summarized in Table 3.

TABLE 3

| | Hole mobility ($\mu_h$) [$10^4 \times cm^2/V \cdot s$] | Electron mobility ($\mu_e$) [$10^4 \times cm^2/V \cdot s$] | $\mu_h/\mu_e$ |
|---|---|---|---|
| PM6:N3 Comp. Experimental Ex. 1 | 2.89 | 1.42 | 2.03 |
| PM6:N3:PY-P2 Experimental Ex. 1 | 5.25 | 4.62 | 1.13 |
| PM6:N3:PY-T1 Experimental Ex. 2 | 2.61 | 1.09 | 2.39 |

As shown in FIG. 4 and Table 3, it was confirmed that the organic solar cells of Experimental Examples 2 and 3 wherein the ternary photoactive layer compositions containing the polymer compounds prepared in Example 2 and Example 3 were used maintained performance similarly to that of Comparative Experimental Example 1.

It was confirmed that the hole mobility and electron mobility of the organic solar cell of Experimental Example 1 wherein the ternary photoactive layer including the polymer compound of Example 1 (PY-P2) was used were 1.8 times and 3.25 times as compared to Comparative Experimental Example 1, respectively.

In particular, whereas the organic solar cell of Comparative Experimental Example 1 wherein the binary photoactive layer was used and the organic solar cells of Experimental Examples 2 and 3 wherein the ternary photoactive layer was used showed a ratio of hole and electron mobilities of 2 or higher, the organic solar cell of Experimental Example 1 maintained a ratio of hole and electron mobilities between 1 and 1.2.

Accordingly, it can be seen that it is preferred to use the polymer compound of Example 1 (PY-P2) in the photoactive layer for preparation of an organic solar cell with superior charge and electron transport characteristics.

Figure 5:
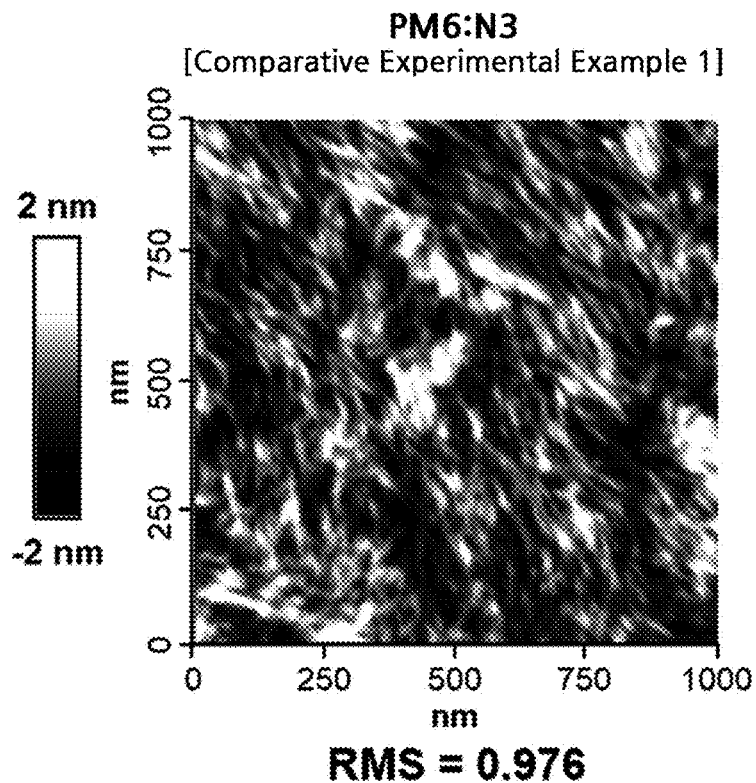
FIG. 5 shows the image of a photoactive layer of an organic solar cell of Comparative Experimental Example 1 obtained by atomic force microscopy (AFM).
Figure 6:
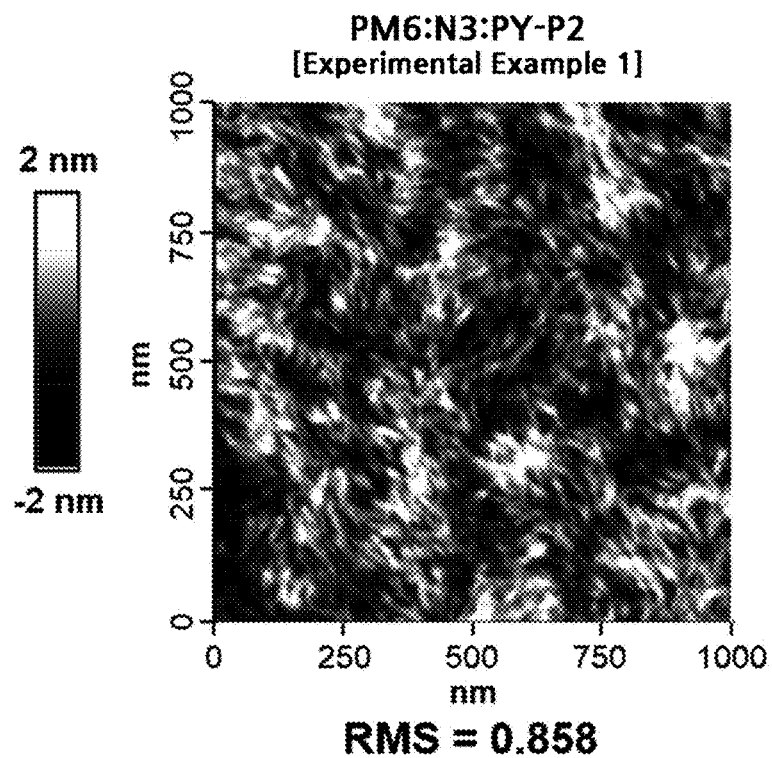
FIG. 6 shows the image of a photoactive layer of an organic solar cell of Experimental Example 1 obtained by atomic force microscopy (AFM).
Figure 7:
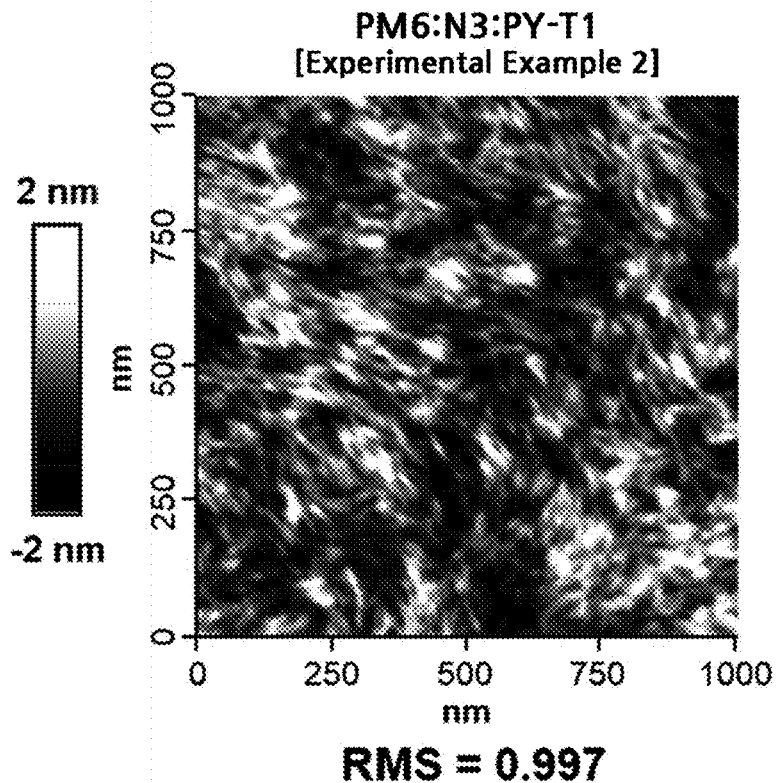
FIG. 7 shows the image of a photoactive layer of an organic solar cell of Experimental Example 2 obtained by atomic force microscopy (AFM).
Figure 8:
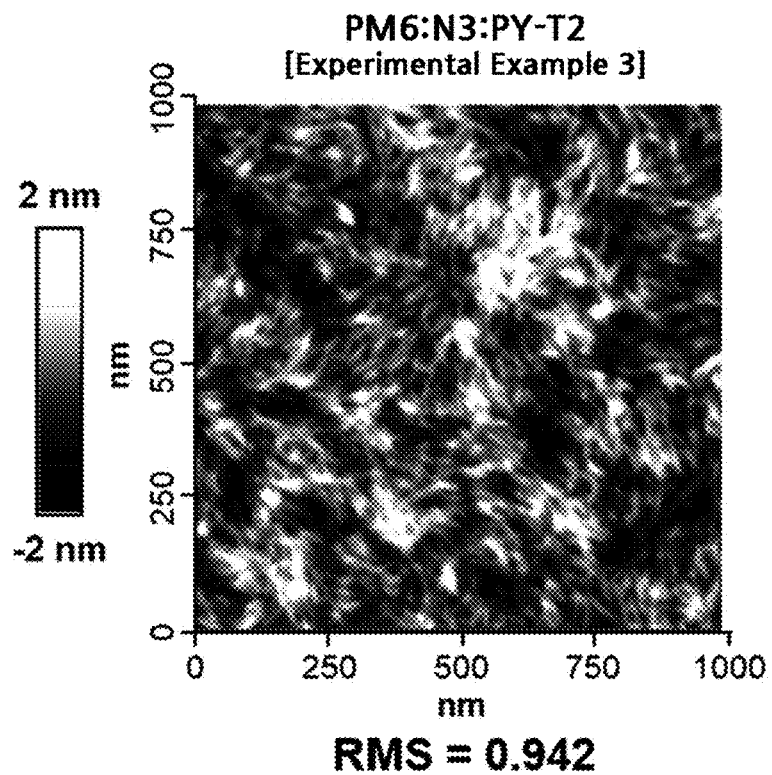
FIG. 8 shows the image of a photoactive layer of an organic solar cell of Experimental Example 3 obtained by atomic force microscopy (AFM).

FIG. 5 shows the atomic force microscopy (AFM) image of the photoactive layer of the organic solar cell of Comparative Experimental Example 1, FIG. 6 shows the atomic force microscopy (AFM) image of the photoactive layer of the organic solar cell of Experimental Example 1, FIG. 7 shows the shows the atomic force microscopy (AFM) image of the photoactive layer of the organic solar cell of Experimental Example 2, and FIG. 8 shows the shows the atomic force microscopy (AFM) image of the photoactive layer of the organic solar cell of Experimental Example 3.

As shown in FIGS. 5-8, it was confirmed that PM6:N3 (Comparative Experimental Example 1), PM6:N3:PY-T1 (Experimental Example 2) and PM6:N3:PY-T2 (Experimental Example 3) have similar surface roughness (RMS: root mean square).

It can be seen that PM6:N3:PY-P2 (Experimental Example 1) has uniform surface with significantly improved surface roughness (RMS: root mean square) as compared to PM6:N3 (Comparative Experimental Example 1). That is to say, it was confirmed that the ternary photoactive layer of PM6:N3:PY-P2 (Experimental Example 1) has the most uniform and smooth surface (The surface roughness was calculated as a RMS (root mean square) value for 1 μm×1 μm from the 3D surface image.).

For analysis of the thermal stability of the organic solar cells of Experimental Example 1, Experimental Example 3 and Comparative Experimental Example 1, the cells were heat-treated at 80° C. for 1000 hours and PCE (power conversion efficiency) value was measured depending on exposure time. The PCE value was normalized and plotted.

Figure 9:
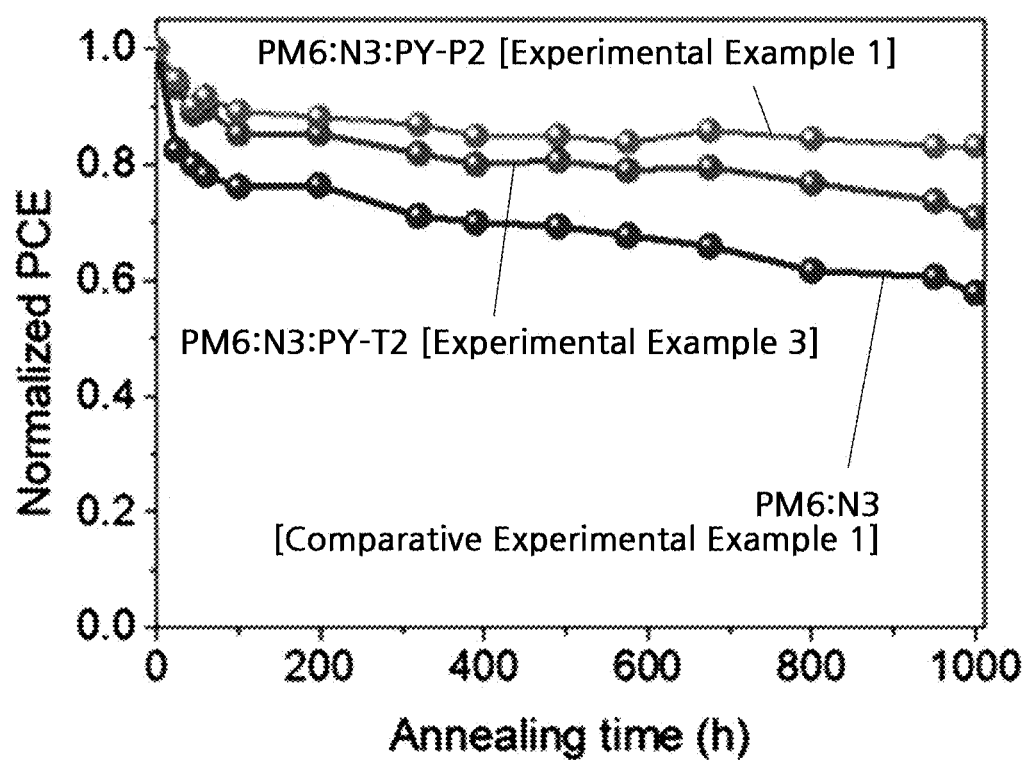
FIG. 9 shows a result of measuring long-term thermal stability for organic solar cells of Experimental Example 2, Experimental Example 3 and Comparative Experimental Example 1.

FIG. 9 shows the normalized PCE values for the organic solar cells of Experimental Example 1, Experimental Example 3 and Comparative Experimental Example 1 depending on exposure time. In the organic solar cell of Comparative Experimental Example 1, wherein only the single-molecule electron acceptor was used, PCE value was decreased significantly from 1.0 to 0.6 due to morphological change. However, the organic solar cells using the ternary photoactive layers (Experimental Examples 1 and 3) showed higher thermal stability than the organic solar cell of Comparative Experimental Example 1 wherein only the single-molecule electron acceptor was used. In particular, the organic solar cell using the ternary photoactive layer wherein PY-P2 was added as the second electron acceptor polymer (Experimental Example 1) maintained 80% of the initial efficiency for 1000 hours. Through this, it can be seen that the PY-P2 second electron acceptor polymer compound significantly improves the thermal stability of the organic solar cell by effectively inhibiting heat-induced morphological change of the first electron acceptor material and the electron donor material.

<Test Example 2> Molecular Modeling Analysis

In order to investigate the effect of the structure of the second electron acceptor polymer during the formation of the ternary photoactive layer, the 3D structure of the second electron acceptor polymers prepared in Preparation Examples 1-3 (PY-P2, PY-T1, PY-T2) was obtained by density functional theory (DFT) (B3LYP hybrid function, 6-31+G(d,p) basis set) using the Gaussian 09 package. Each module investigated 5 or more times to ensure the docking result. The molecular modeling result for the second electron acceptor polymer compounds prepared in Preparation Examples 1-3 (PY-P2, PY-T1, PY-T2) is shown in FIGS. 10A to 10C.

Figure 10A:
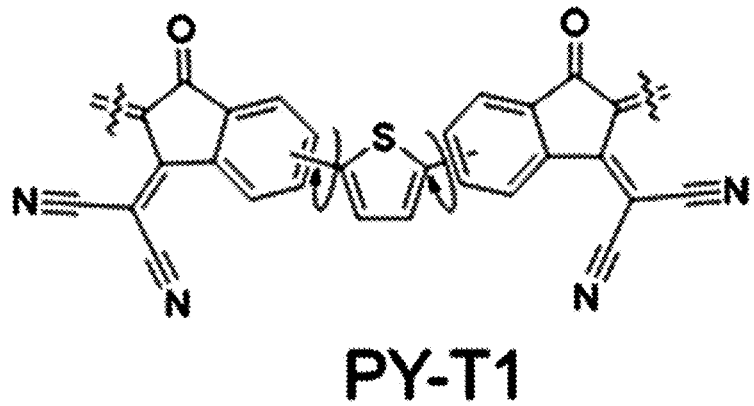
FIGS. 10A to 10C show the modeled structures and torsional angles of second electron acceptor compounds (PY-P2 (FIG. 10C), PY-T1 (FIG. 10A), PY-T2 (FIG. 10B)) prepared in Preparation Examples 1-3.
Figure 10B:
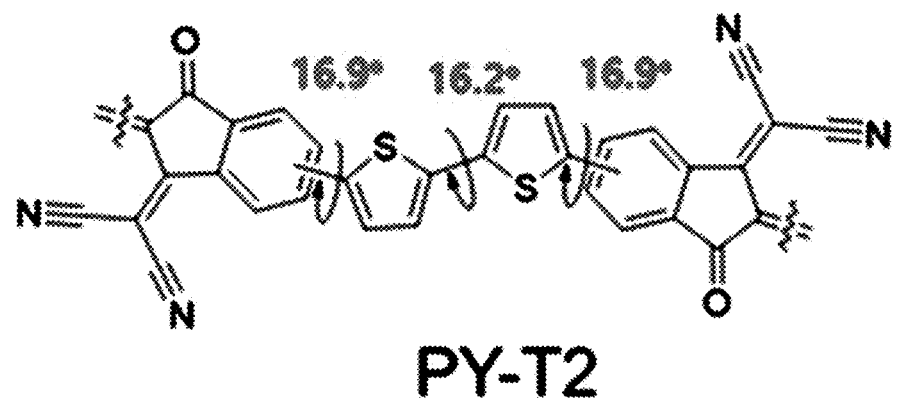
Figure 10C:
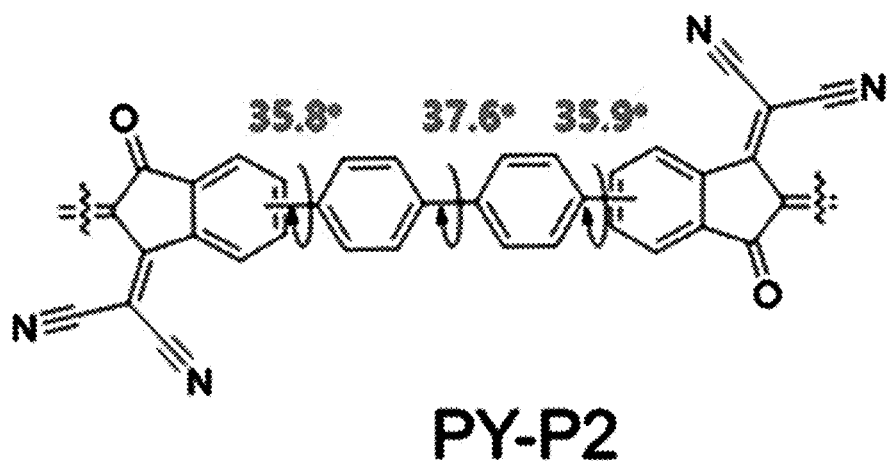

FIGS. 10A to 10C show the modeled structures and torsional angles of the second electron acceptor polymer compounds prepared in Preparation Examples 1-3 (PY-P2 (FIG. 10C), PY-T1 (FIG. 10A), PY-T2 (FIG. 10B)).

As shown in FIGS. 10A to 10C, it was confirmed that the diphenyl functional group contained in the second electron acceptor polymer compound prepared in Preparation Example 1 (PY-P2 (c)) has a large torsional angle of 35.8-37.6°.

In contrast, the torsional angles of the second electron acceptor polymer compounds prepared in Preparation Examples 2-3 (PY-T1 (a), PY-T2 (b)) was half or smaller as 16.9°. That is to say, it can be seen that, in order to achieve the remarkable effect of the ternary photoactive layer as in the present disclosure, it is preferred to use the second electron acceptor polymer compound prepared in Preparation Example 1 (PY-P2 (c)), which has a large torsional angle.

Whereas the second electron acceptor polymer compound prepared in Preparation Example 1 (PY-P2 (c)) exhibits superior solubility and processability due to the large torsional angle, PY-T1 (a) and PY-T2 (b) having a small torsional angle exhibit low processability and solubility.

What is claimed is:

1. A ternary photoactive layer composition for an organic solar cell, comprising:
    a first electron acceptor material;
    a second electron acceptor compound represented by Chemical Formula I; and
    an electron donor material:

[Chemical Formula I]

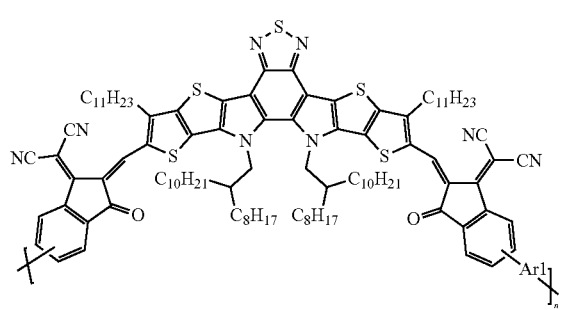

wherein $Ar_1$ is one selected from [Structural Formula 1] and n is an integer in a range from 1 to 1000:

[Structural Formula 1]

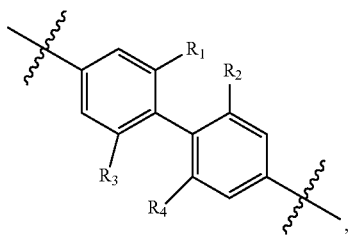

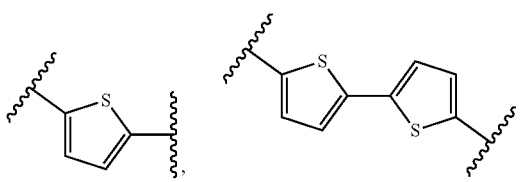

wherein each of $R_1$, $R_2$, $R_3$ and $R_4$, which are identical to or different from each other, is independently one selected from hydrogen, a halogen and a $C_{1-4}$ alkyl group.

2. The ternary photoactive layer composition according to claim 1, wherein the first electron acceptor material and the second electron acceptor compound are mixed at 50-150 parts by weight and 1-50 parts by weight, respectively, based on 100 parts by weight of the electron donor material.

3. The ternary photoactive layer composition according to claim 1, wherein Chemical Formula I is one selected from Chemical Formulas Ia to Ic:

[Chemical Formula Ia]

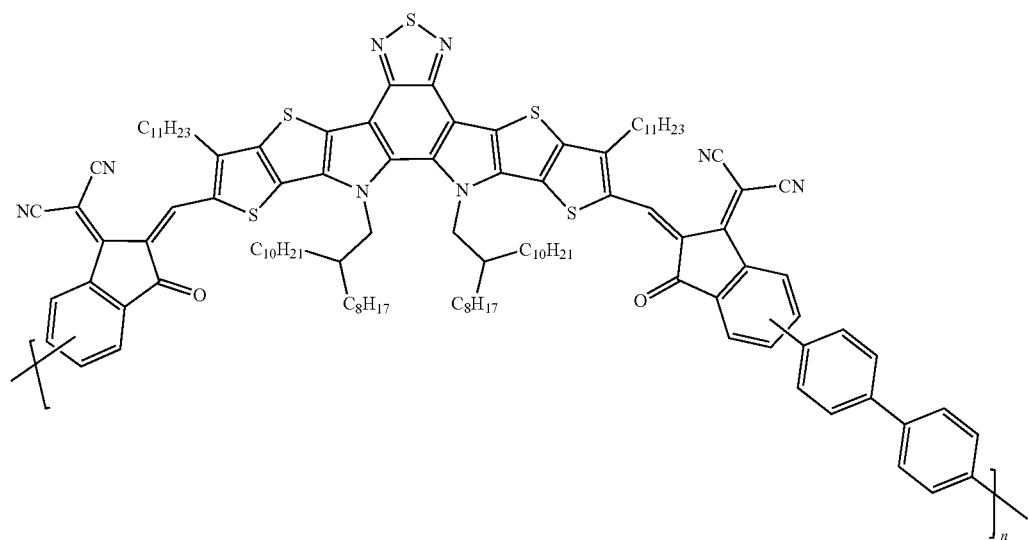

[Chemical Formula Ib]
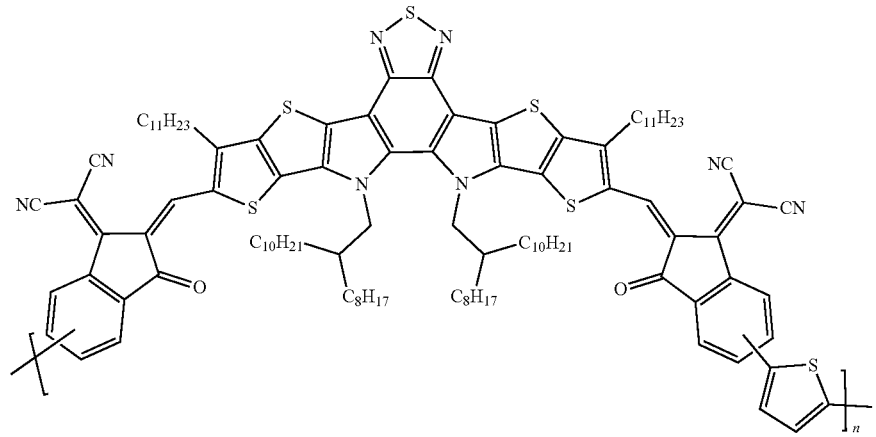
[Chemical Formula Ic]
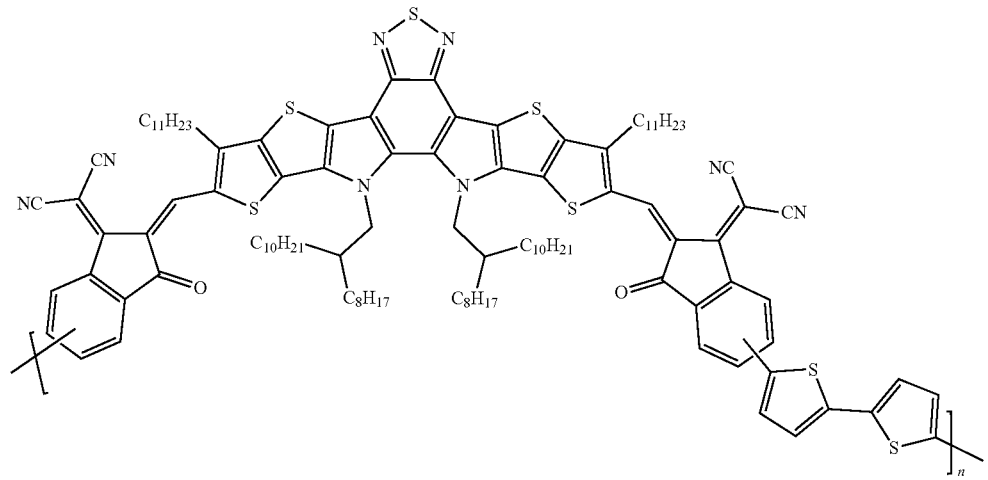
wherein n is an integer in a range from 1 to 1000.

4. The ternary photoactive layer composition according to claim 1, wherein Chemical Formula I is Chemical Formula Ia:

[Chemical Formula Ia]

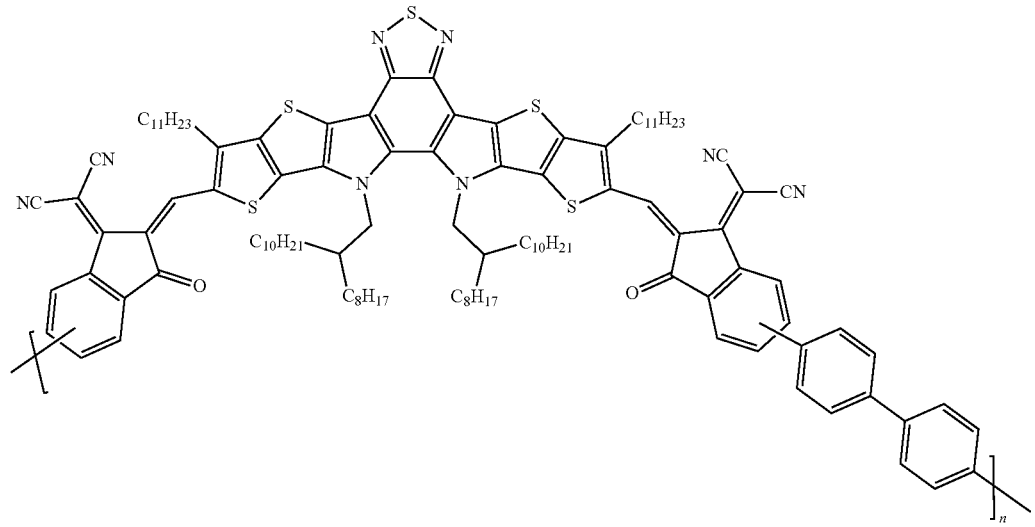

wherein n is an integer in a range from 1 to 1000.

5. The ternary photoactive layer composition according to claim 1, wherein the first electron acceptor material is one or more selected from a group consisting of fullerene, 6,6-phenyl-C61-butyric acid methyl ester (PCBM(C61)), PCBM(C60), PCBM(C70), PCBM(C71), PCBM(C76), PCBM(C80), PCBM(C82), indene-$C_{60}$ bisadduct (ICBA), 6,6-phenyl-$C_{61}$-butyric acid cholesteryl ester (PCBCR), polybenzimidazole, perylene, poly[[N,N'-bis(2-octyldodecyl)-napthalene-1,4,5,8-bis(dicarboximide)-2,6-diyl]-alt-5,5'-(2,2'-bithiophene)] (NDI2OD-T2), naphthalene diimide (NDI)-selenophene copolymer (PNDIS-HD), poly[(E)-2,7-bis(2-decyltetradecyl)-4-methyl-9-(5-(2-(5-methylthiophen-2-yl)vinyl)thiophen-2-yl)benzo[lmn][3,8]phenanthroline-1,3,6,8(2H,7H)-tetraone] (PNDI-TVT), poly[[N,N'-bis(2-hexyldecyl)naphthalene1,4,5,8-bis(dicarboximide)-2,6-diyl]-alt-5,5'-thiophene] (PNDI2HD-T), 3,9-bis(2-methylene-(3-(1,1-dicyanomethylene)-indanone))-5,5,11,11-tetrakis(4-hexylphenyl)-dithieno[2,3-d:2',3'-d']-s-indaceno[1,2-b:5,6-b']dithiophene (ITIC), 3,9-bis(2-methylene-(3-(1,1-dicyanomethylene)-indanone))-5,5,11,11-tetrakis(5-hexylthienyl)-dithieno[2,3-d:2',3'-d']-s-indaceno[1,2-b:5,6-b']dithiophene (ITIC-Th), 2,7-bis(3-dicyanomethylene-2Z-methylene-indan-1-one)-4,4,9,9-tetrahexyl-4,9-dihydro-s-indaceno[1,2-b:5,6-b']dithiophene (IDIC), 3,9-bis(2-methylene-((3-(1,1-dicyanomethylene)-6,7-difluoro)-indanone))-5,5,11,11-tetrakis(4-hexylphenyl)-dithieno[2,3-d:2',3'-d']-s-indaceno[1,2-b:5,6-b']dithiophene (ITIC-4F), 2,2'-((2Z,2'Z)-(((4,4,9-tris(4-hexylphenyl)-9-(4-pentylphenyl)-4,9-dihydro-s-indaceno[1,2-b:5,6-b-dithiophene-2,7-diyl)bis(4-((2-ethylhexyl)oxy)thiophene-5,2-diyl))bis(methanylidene))bis(5,6-difluoro-3-oxo-2,3-dihydro-1H-indene-2,1-diylidene))dimalononitrile (IEICO-4F), 2,2'-((2Z,2'Z)-(((4,4,9-tris(4-hexylphenyl)-9-(4-pentylphenyl)-4,9-dihydro-s-indaceno[1,2-b:5,6-b-dithiophene-2,7-diyl)bis(4-((2-ethylhexyl)oxy)thiophene-5,2-diyl))bis(methanylidene))bis(5,6-dichloro-3-oxo-2,3-dihydro-1H-indene-2,1-diylidene))dimalononitrile (IEICO-4C1), 2,2'-((2Z,2'Z)-((12,13-bis(2-ethylhexyl)-3,9-diundecyl-12,13-dihydro-[1,2,5]thiadiazolo[3,4-e]thieno [2",3":4',5']thieno[2',3':4,5]pyrrolo[3,2-g]thieno[2',3':4,5] thieno[3,2-b]indole-2,10-diyl)bis(methanylidene))bis(5,6-difluoro-3-oxo-2,3-dihydro-1H-indene-2,1-diylidene)) dimalononitrile (Y6 or BTP-4F), 2,2'-((2Z,2'Z)-((12,13-bis (2-ethylhexyl)-3,9-diundecyl-12,13-dihydro-[1,2,5] thiadiazolo[3,4-e]thieno[2",3":4',5']thieno[2',3':4,5]pyrrole [3,2-g]thieno[2',3':4,5]thieno[3,2-b]indole-2,10-diyl)bis (methanylidene))bis(5,6-dichloro-3-oxo-2,3-dihydro-1H-indene-2,1-diylidene))dimalononitrile (Y7 or BTP-4C1) and Y6-N3.

6. The ternary photoactive layer composition according to claim 1, wherein the electron donor material is one or more selected from a group consisting of poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]] (PTB7), poly[3,6-bis(5-thiophen-2-yl)-2,5-bis (2-octyldodecyl)pyrrolo[3,4-c]pyrrole-1,4(2H,5H)-dione-2,2'-diyl-alt-thieno[3,2-b]thiophen2,5-diyl] (PDPP2T-TT), poly(3-octylthiophene-2,5-diyl)(P3OT), poly(p-phenylene vinylene) (PPV), poly(dioctyl fluorene), poly[2-methoxy-5-(2-ethylhexyloxy)-1,4-phenylenevinylene] (MEHPPV), poly[2-methoxy-5-(3',7'-dimethyloctyloxy)-1,4-phenylenevinylene] (MDMO-PPV), poly[2,6-(4,4-bis-(2-ethylhexyl)-4H-cyclopenta [2,1-b;3,4-b']dithiophene)-alt-4,7(2,1,3-benzothiadiazole)] (PCPDTBT), poly[4,8-bis(5-(2-ethylhexyl)thiophen-2-yl)-benzo[1,2-b:4,5-b']dithiophene-alt-5-octyl-4H-thieno[3,4-6-c]pyrrole-4,6(5H)-dione] (PBDTTTPD), poly[(2,5-bis(2-hexyldecyloxy)phenylene)-alt-(5,6-difluoro-4,7-di(thiophen-2-yl)benzo-[c][1,2,5]thiadiazole)] (PPDT2FBT), poly(3-hexylthiophene)(P3HT), poly{1-(5-(4,8-bis(5-(2-ethylhexyl)thiophen-2-yl)-6-methylbenzo[1,2-b:4,5-b']-dithiophen-2-yl)thiophen-2-yl)-5,7-bis(2-ethylhexyl)-3-(5-methylthiophen-2-yl)benzo-[1,2-c:4,5-c']dithiophene-4,8-dione} (PBDTBDDT) and poly[(2,6-(4,8-bis(5-(2-ethylhexyl-3-fluoro)thiophen-2-yl)-benzo[1,2-b:4,5-b']dithiophene))-alt-(5,5-(1',3'-di-2-thienyl-5',7'-bis(2-ethylhexyl)benzo[1',2'-c:4',5'-c']dithiophene-4,8-dione)] (PBDB-TF, PM6).

7. The ternary photoactive layer composition according to claim 1, wherein the ternary photoactive layer composition may further comprise one or more selected from a group consisting of chlorobenzene, chloroform, p-xylene, 1,2-dichlorobenzene, trichlorobenzene, toluene, chloronaphthalene and 1,8-diiodooctane as a solvent.

8. The ternary photoactive layer composition according to claim 7, wherein the solvent is a mixture of chloroform and 1-chloronaphthalene at a volume ratio of 0.995:0.001-0.01.

9. An organic solar cell comprising:
a first electrode;
an electron transport layer formed on the first electrode;
a photoactive layer comprising the composition according to claim 1 and formed on the electron transport layer;
a hole transport layer formed on the photoactive layer; and
a second electrode formed on the hole transport layer.

10. The organic solar cell according to claim 9, wherein the electron transport layer comprises one or more selected from a group consisting of ZnO, LiF, $TiO_x$, $TiO_2$, $CsCO_3$ and Ca.

11. The organic solar cell according to claim 9, wherein the photoactive layer has a bulk hetero junction structure in which the first electron acceptor material, the second electron acceptor compound and the electron donor material are mixed.

12. The organic solar cell according to claim 9, wherein the orientation and crystallinity of molecules comprised in the photoactive layer are controlled by the second electron acceptor compound.

13. The organic solar cell according to claim 9, wherein the hole transport layer comprises one or more selected from a group consisting of molybdenum oxide ($MoO_2$, $MoO_3$), PEDOT:PSS (poly(3,4-ethylenedioxythiophene) polystyrene sulfonate), tungsten oxide ($WO_3$), nickel oxide and cerium-doped tungsten oxide ($CeWO_3$).

14. The organic solar cell according to claim 9, wherein the first electrode comprises one or more selected from a group consisting of indium tin oxide (ITO), fluorine tin oxide (FTO), silver (Ag) nanowire and silver nanomesh.

15. The organic solar cell according to claim 9, wherein the second electrode comprises one or more selected from a group consisting of Au, Fe, Ag, Cu, Cr, W, Al, Mo, Zn, Ni, Pt, Pd, Co, In, Mn, Si, Ta, Ti, Sn, Pb, V, Ru, Ir, Zr, Rh, $MoO_3$ and Mg.

16. A vehicle adopting the organic solar cell according to claim 9.

* * * * *